US008507736B2

(12) United States Patent
Hulteberg et al.

(10) Patent No.: US 8,507,736 B2
(45) Date of Patent: Aug. 13, 2013

(54) GAS PHASE PROCESS FOR MONOALCOHOL PRODUCTION FROM GLYCEROL

(75) Inventors: Christian Hulteberg, Limhamn (SE); Jan Brandin, Limhamn (SE); Richard R. Woods, Irvine, CA (US); Brook Porter, Playa Vista, CA (US)

(73) Assignee: BioFuel-Solution i Malmo AB, Limhamn (SE)

( * ) Notice: Subject to any disclaimer, the term of this patent is extended or adjusted under 35 U.S.C. 154(b) by 1118 days.

(21) Appl. No.: 12/121,728

(22) Filed: May 15, 2008

(65) Prior Publication Data

US 2009/0005614 A1    Jan. 1, 2009

Related U.S. Application Data

(60) Provisional application No. 60/930,704, filed on May 18, 2007, provisional application No. 61/023,816, filed on Jan. 25, 2008.

(51) Int. Cl.
*C07C 29/14*    (2006.01)

(52) U.S. Cl.
USPC .......................................... 568/903; 568/471

(58) Field of Classification Search
USPC ................. 568/903, 471; 549/454; 205/441; 560/212
See application file for complete search history.

(56) References Cited

U.S. PATENT DOCUMENTS

| | | | |
|---|---|---|---|
| 2,139,351 A * | 12/1938 | Bejarano ........................ | 585/263 |
| 3,173,959 A | 3/1965 | Rittmeister | |
| 3,832,392 A | 8/1974 | Imamura et al. | |
| 4,032,458 A | 6/1977 | Cooley et al. | |
| 4,036,905 A | 7/1977 | Kornfeld | |
| 4,049,576 A | 9/1977 | Kovach et al. | |
| 4,261,700 A | 4/1981 | Monick et al. | |
| 4,369,096 A | 1/1983 | Seifert et al. | |
| 4,658,068 A | 4/1987 | Hanin | |
| 4,837,367 A * | 6/1989 | Gustafson et al. ............ | 568/831 |
| 5,004,845 A | 4/1991 | Bradley et al. | |
| 5,214,219 A | 5/1993 | Casale et al. | |
| 5,387,720 A * | 2/1995 | Neher et al. .................. | 568/486 |
| 5,426,249 A * | 6/1995 | Haas et al. .................... | 568/862 |
| 5,684,215 A * | 11/1997 | Horn et al. .................... | 568/881 |
| 5,865,985 A | 2/1999 | Desai et al. | |
| 5,990,323 A | 11/1999 | Clubb | |
| 6,562,315 B2 | 5/2003 | Korotkikh et al. | |
| 7,201,783 B2 | 4/2007 | Edlund | |
| 2003/0220531 A1 | 11/2003 | Cortright et al. | |
| 2005/0004401 A1 | 1/2005 | Barnicki et al. | |
| 2006/0057058 A1 | 3/2006 | Dahl et al. | |
| 2006/0258892 A1 | 11/2006 | Yamamoto et al. | |
| 2007/0101640 A1 | 5/2007 | Tsuto et al. | |

FOREIGN PATENT DOCUMENTS

| | | |
|---|---|---|
| EP | 1 970 368 A1 | 9/2008 |
| GB | 640260 | 7/1950 |
| WO | 2006/087083 A2 | 8/2006 |
| WO | 2006/087084 A2 | 8/2006 |
| WO | WO 2007/053705 | 5/2007 |

OTHER PUBLICATIONS

Tanabe et al; Book Chapters 1-2, New Solid acids and bases, their catalytic properties, Elsevier Science Publishers B.V.. 1989.*
Baba et al; Journal of Molecular catalysis A: Chemical 114 (1996) 247-255.*
International Search Report issued in corresponding International Application No. PCT/US2008/63798 filed May 15, 2008.
Written Opinion issued in corresponding International Application No. PCT/US2008/63798 filed May 15, 2008.
International Search Report for International Application No. PCT/EP2009/064517 mailed May 20, 2010, corresponding to U.S. Appl. No. 13/127,599.
Ratna Shekhar et al., "Decarbonylation and hydrogenation reactions of allyl alcohol and acrolein on Pd(110)", Surface Science 319, 1994, pp. 298-314.
Aharon Oren, "A hundred years of *Dunaliella* research: 1905-2005", Saline Systems 2005, 1:2 (doi:10.1186/1746-1448-1-2), 14 pages.
Taherzadeh et al., "Strategies for enhancing fermentative production of glycerol—1 review", Enzyme and Microbial Technology 31, 2002, pp. 53.66.
PCT International Preliminary Report on Patentability issued in corresponding International Application No. PCT/US2008/63798 dated Nov. 24, 2009.
Jungermann, et al., "Glycerine: A Key Cosmetic Ingredient," table of contents, chapter 5 and chapter 7, New York, (1991).
Juan Carlos de Jesus and Francisco Zaera, "Double-Bond Activation in Unsaturated Aldehydes: Conversion of Acrolein to Propene and Ketene on Pt(111) Surfaces," Journal of Molecular Catalysis, vol. 138, 1999, pp. 237-240.
V. V. Brei, D. V. Shistka and A. G. Grebenyuk, "Symbatic Relationship Between Proton Affinity and Ease of Dehydration and Dealkylation of Alcohol and Alkylbenzene Molecules on Acid Catalysts," Theoretical and Experimental Chemistry, vol. 40, No. 3, 2004, pp. 192-197.
Alessandro Trovarelli, "Catalytic Properties of Ceria and $CeO_2$-Containing Materials," Catalysis Reviews: Science and Engineering, vol. 38, Issue 4, 1996, pp. 439-470.
Klaus-Dieter Henkel, "Reactor Types and Their Industrial Applications," Ullmann's Encyclopedia of Industrial Chemistry, Wiley-VCH, vol. 31, published online Jun. 2000, pp. 293-327.
Baba et al., "H NMR studies on the dynamic property of protons in $Pd^0$-$H_3PW_{12}O_{40}$ systems in the presence of dihydrogen", Journal of Molecular Catalysis A: Chemical 114 (1996), pp. 247.255.
Tanabe et al., Chapters 1-2, New solid acids and bases, their catalytic properties, Elsevier Science Publishers B.V., 1989.

* cited by examiner

*Primary Examiner* — Johann R Richter
*Assistant Examiner* — Pancham Bakshi
(74) *Attorney, Agent, or Firm* — Renner, Otto, Boisselle & Sklar, LLP

(57) ABSTRACT

A method of producing short chain alcohols from glycerol generated as a byproduct of biodiesel production is provided.

26 Claims, 17 Drawing Sheets

US 8,507,736 B2

GAS PHASE PROCESS FOR MONOALCOHOL PRODUCTION FROM GLYCEROL

CROSS-REFERENCE TO RELATED APPLICATIONS

This application claims the benefit under 35 U.S.C. §119(e) of U.S. Provisional Application No. 60/930,704, filed on May 18, 2007 and U.S. Provisional Application No. 61/023,816, filed on Jan. 25, 2008; the disclosures of each of which are hereby expressly incorporated by reference in their entireties and are hereby expressly made a portion of this application.

FIELD OF THE INVENTION

A method of producing short chain alcohols from glycerol generated as a byproduct of biodiesel production is provided.

BACKGROUND OF THE INVENTION

Biodiesel is a fuel derived from vegetable oils or animal fats. In use, it has similar properties as conventional (petroleum-based) diesel fuel. A common form of biodiesel includes the methyl ester or ethyl ester of fatty acids obtained from vegetable oil or animal fat. Vegetable oils and animal fats are generally triglycerides. Biodiesel is usually produced either by the direct esterification of fatty acids or by the transesterification of the source oil.

Glycerol is a byproduct of the production of fatty acids and of the transesterification process used to produce biodiesel. Depending on the particular fat or oil used as the biodiesel source, glycerol as a byproduct can comprise up to approximately 9-11 wt. % of the starting material.

Several markets already exist for glycerol as a byproduct of fatty acid or biodiesel production. Glycerol is a common feedstock in the synthesis of various chemicals, and has a number of uses in pharmaceutical formulations. However, these markets typically require highly purified glycerol. Such purification can be costly and must be done in a large-scale operation to be profitable. In addition, as the volume of biodiesel production (and thus byproduct glycerol production) increases, existing markets for glycerol are becoming saturated and the price paid for the glycerol will decrease, adversely impacting the economics of biodiesel production.

In addition, the need to supply raw material monohydric alcohols to a biodiesel production facility, and the simultaneous need to ship out side product glycerol from the facility can increase the cost for the biodiesel produced and can limit the facility siting geographically to those locations with good and inexpensive transport as well as proximity to markets for the glycerol and supplies for the alcohols. Further, because the price paid for the glycerol depends on the use it is put to, acceptable facility siting can be limited even further to those locations readily accessible to facilities that will pay a premium for the glycerol, such as pharmaceutical, cosmetic, and personal care facilities.

In addition, the transport itself of the alcohols and the glycerol is an undesirable aspect of many proposed biodiesel facilities. Such transport increases the consumption of motor fuels which increases air pollution and can lead to other environmental problems. Use of the glycerol on site as a valuable material can reduce these unfortunate problems with conventional biodiesel operations.

Finally, the need to supply monohydric alcohol from outside sources to a biodiesel facility means that other resources will be needed to support the biodiesel production at that facility. If instead, this raw material can be produced on-site from materials that are readily available at the location, fewer outside resources will be needed to support the facility and resulting in a smaller environmental footprint for the facility.

SUMMARY OF THE INVENTION

An economically viable use for glycerol produced as a byproduct of biodiesel production is highly desirable. A method is provided for converting glycerol to monohydric alcohols, which are a valuable feedstock in the production of biodiesel.

Accordingly, in a first aspect a method is provided for producing a monohydric alcohol from glycerol, the method comprising reacting a gas phase mixture comprising glycerol and hydrogen in a presence of a heterogeneous catalyst system to yield a reaction mixture comprising at least one carbonyl compound, wherein the heterogeneous catalyst system comprises a dehydration catalyst and a hydrogenation catalyst, and wherein conditions of the dehydration reaction and conditions of the hydrogenation reaction are controlled such that a heat required by the dehydration reaction balances a heat generated by the hydrogenation reaction; and reacting a mixture comprising hydrogen and at least a portion of the reaction mixture comprising at least one carbonyl compound over a hydrogenation catalyst to yield a reaction stream comprising at least one monohydric alcohol.

In an embodiment of the first aspect, an absolute value of the heat required by the dehydration reaction is provided by an absolute value of the heat generated by the hydrogenation reaction.

In an embodiment of the first aspect, an absolute value of the heat generated by the hydrogenation reaction provides an absolute value of the heat required by the dehydration reaction and additional heat for other processes.

In an embodiment of the first aspect, the heterogeneous catalyst system comprises a first portion and a second portion, the first portion comprising a mixture of dehydration catalyst and hydrogenation catalyst, wherein the hydrogenation catalyst and the dehydration catalyst are different from each other.

In an embodiment of the first aspect, the heterogeneous catalyst system comprises a first portion and a second portion, the first portion has a first dehydration activity and a first hydrogenation activity and comprises a mixture of dehydration catalyst and hydrogenation catalyst, wherein the hydrogenation catalyst and the dehydration catalyst are different from each other; the second portion of the heterogeneous catalyst system has a second dehydration activity and a second hydrogenation activity, and wherein a ratio of the first hydrogenation activity to the first dehydration activity is less than a ratio of the second hydrogenation activity to the second dehydration activity.

In an embodiment of the first aspect, the heterogeneous catalyst system comprises a first portion and a second portion, the first portion has a first dehydration activity and a first hydrogenation activity and comprises a mixture of dehydration catalyst and hydrogenation catalyst, wherein the hydrogenation catalyst and the dehydration catalyst are different from each other; the second portion of the heterogeneous catalyst system has a second dehydration activity and a second hydrogenation activity, and wherein a ratio of the first hydrogenation activity to the first dehydration activity is less than a ratio of the second hydrogenation activity to the second dehydration activity and a ratio of the first hydrogenation activity to the second hydrogenation activity is from about 0:1 to about 1:5.

In an embodiment of the first aspect, the heterogeneous catalyst system comprises a first portion and a second portion, the first portion has a first dehydration activity and a first hydrogenation activity and comprises a mixture of dehydration catalyst and hydrogenation catalyst, wherein the hydrogenation catalyst and the dehydration catalyst are different from each other; the second portion of the heterogeneous catalyst system has a second dehydration activity and a second hydrogenation activity, and wherein a ratio of the first hydrogenation activity to the first dehydration activity is less than a ratio of the second hydrogenation activity to the second dehydration activity, and a ratio of the first hydrogenation activity to the first dehydration activity is from about 0:1 to about 1:5.

In an embodiment of the first aspect, the heterogeneous catalyst system comprises a first portion and a second portion, the first portion has a first dehydration activity and a first hydrogenation activity and comprises a mixture of dehydration catalyst and hydrogenation catalyst, wherein the hydrogenation catalyst and the dehydration catalyst are different from each other; the second portion of the heterogeneous catalyst system has a second dehydration activity and a second hydrogenation activity, and wherein a ratio of the first hydrogenation activity to the first dehydration activity is less than a ratio of the second hydrogenation activity to the second dehydration activity; wherein the gas phase mixture comprising glycerol and hydrogen is exposed to the first portion to produce an intermediate stream, and the intermediate stream is exposed to the second portion.

In an embodiment of the first aspect, the heat required by the dehydration reaction and the heat generated by the hydrogenation reaction are balanced by controlling a ratio of an amount of dehydration catalyst to an amount of hydrogenation catalyst in the heterogeneous catalyst system.

In an embodiment of the first aspect, a molar ratio of hydrogen to glycerol in the gas phase mixture is from about 0.05:10 to about 2:1.

In an embodiment of the first aspect, a molar ratio of hydrogen to glycerol in the gas phase mixture is from about 0.1:10 to about 3:2.

In an embodiment of the first aspect, the heat required by the dehydration reaction and the heat generated by the hydrogenation reaction are balanced by controlling a ratio of hydrogen to glycerol.

In an embodiment of the first aspect, an amount of hydrogen in the mixture comprising hydrogen and at least a portion the carbonyl compound is such that hydrogen is present in excess of a stoichiometric amount necessary for conversion of all carbonyl groups present in the mixture to hydroxyl groups.

In an embodiment of the first aspect, an amount of hydrogen in the mixture comprising hydrogen and at least a portion the carbonyl compound is such that hydrogen is present at least 10% in excess of a stoichiometric amount necessary for conversion of all carbonyl groups present in the mixture to hydroxyl groups.

In an embodiment of the first aspect, an amount of hydrogen in the mixture comprising hydrogen and at least a portion the carbonyl compound is such that hydrogen is present at least 20% in excess of a stoichiometric amount necessary for conversion of all carbonyl groups present in the mixture to hydroxyl groups.

In an embodiment of the first aspect, an amount of hydrogen in the mixture comprising hydrogen and at least a portion the carbonyl compound is such that hydrogen is present at least 30% in excess of a stoichiometric amount necessary for conversion of all carbonyl groups present in the mixture to hydroxyl groups.

In an embodiment of the first aspect, an amount of hydrogen in the mixture comprising hydrogen and at least a portion the carbonyl compound is such that hydrogen is present from about 40% to about 150% in excess of a stoichiometric amount necessary for conversion of all carbonyl groups present in the mixture to hydroxyl groups.

In an embodiment of the first aspect, the gas phase mixture comprising glycerol and hydrogen further comprises water.

In an embodiment of the first aspect, the gas phase mixture comprising glycerol and hydrogen further comprises water, and the water and glycerol are present in the gas phase mixture in a weight ratio of from about 3:1 to about 9:1.

In an embodiment of the first aspect, the gas phase mixture comprising glycerol and hydrogen further comprises water, and the water and glycerol are present in the gas phase mixture in a weight ratio of from about 4:1 to about 6:1.

In an embodiment of the first aspect, the gas phase mixture comprising glycerol and hydrogen further comprises water, and the water comprises from about 60 wt. % to about 90 wt. % of the gas phase mixture.

In an embodiment of the first aspect, the gas phase mixture comprising glycerol and hydrogen further comprises water, and the water comprises from about 70 wt. % to about 90 wt. % of the gas phase mixture.

In an embodiment of the first aspect, glycerol comprises from about 10 wt. % to about 40 wt. % wt. of the gas phase mixture.

In an embodiment of the first aspect, glycerol comprises from about 15 wt. % to about 25 wt. % wt. of the gas phase mixture.

In an embodiment of the first aspect, the gas phase mixture is reacted at a temperature of from about 260° C. to about 340° C. and at a pressure of from about 0.5 bar to about 10 bar, and the reaction stream comprises a mixture of ethanol, methanol, and propanol.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream.

In an embodiment of the first aspect, the gas phase mixture is reacted at a temperature of from about 260° C. to about 340° C. and a pressure of about 0.5 bar to about 10 bar, and propanol makes up more than about 60% of the total mass of monohydric alcohols in the reaction stream.

In an embodiment of the first aspect, the gas phase mixture is reacted at a temperature of from about 260° C. to about 340° C. and a pressure of about 0.5 bar to about 10 bar, and propanol makes up about 70% to about 100% of the total mass of monohydric alcohols in the reaction stream.

In an embodiment of the first aspect, the gas phase mixture is reacted at a temperature of from about 260° C. to about 340° C. and a pressure of about 0.5 bar to about 10 bar, and propanol makes up about 80% to about 100% of the total mass of monohydric alcohols in the reaction stream.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and water is removed from the reaction mixture comprising at least one carbonyl compound prior to reacting hydrogen and at least a portion of the reaction mixture over the hydrogenation catalyst.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and from about 10% to about 100% of the water present in the reaction mixture comprising at least one carbonyl compound is removed prior to reacting hydrogen and at least a portion of the reaction mixture over the hydrogenation catalyst.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and from about 50% to about 90% of the water present in the reaction mixture comprising at least one carbonyl compound is removed prior to reacting hydrogen and at least a portion of the reaction mixture over the hydrogenation catalyst.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and from about 60% to about 80% of the water present in the reaction mixture comprising at least one carbonyl compound is removed prior to reacting hydrogen and at least a portion of the reaction mixture over the hydrogenation catalyst.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; the reaction mixture comprising at least one carbonyl compound comprises at least one aldehyde; water is removed from the reaction mixture comprising at least one carbonyl compound prior to reacting hydrogen and at least a portion of the reaction mixture over the hydrogenation catalyst; and a weight ratio water to aldehyde present after removing water is from about 20:80 to about 1:99.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; the reaction mixture comprising at least one carbonyl compound comprises at least one aldehyde; water is removed from the reaction mixture comprising at least one carbonyl compound prior to reacting hydrogen and at least a portion of the reaction mixture over the hydrogenation catalyst; and a weight ratio water to aldehyde present after removing water is from about 10:90 to about 1:99.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; the reaction mixture comprising at least one carbonyl compound comprises at least one aldehyde which is propionaldehyde; water is removed from the reaction mixture comprising at least one carbonyl compound prior to reacting hydrogen and at least a portion of the reaction mixture over the hydrogenation catalyst; and a weight ratio water to propionaldehyde present after removing water is from about 10:90 to about 1:99.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; the reaction mixture comprising at least one carbonyl compound comprises at least one aldehyde which is propionaldehyde, and the propionaldyde makes up from about 80 wt. % to about 100 wt. % of the aldehydes present in the reaction mixture comprising at least one carbonyl compound; water is removed from the reaction mixture comprising at least one carbonyl compound prior to reacting hydrogen and at least a portion of the reaction mixture over the hydrogenation catalyst; and a weight ratio water to propionaldehyde present after removing water is from about 10:90 to about 1:99.

In an embodiment of the first aspect, the gas phase mixture is reacted at a temperature of from about 260° C. to about 340° C. and a pressure of about 0.5 bar to about 10 bar, and propanol makes up from about 70 wt. % to about 100 wt. % of the monohydric alcohols present in the reaction stream; and water is removed from the reaction mixture comprising at least one carbonyl compound prior to reacting hydrogen and at least a portion of the reaction mixture over the hydrogenation catalyst.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; water is removed from the reaction mixture comprising at least one carbonyl compound prior to reacting hydrogen and at least a portion of the reaction mixture over the hydrogenation catalyst; and a weight ratio of water to glycerol in the gas phase mixture comprising glycerol and hydrogen is from about 4:1 to about 8:1.

In an embodiment of the first aspect, the gas phase mixture is reacted at a temperature of from about 280° C. to about 320° C. and a pressure of about 5 bar to about 7 bar, and propanol makes up more than about 50% of the total mass of monohydric alcohols in the reaction stream; water is removed from the reaction mixture comprising at least one carbonyl compound prior to reacting hydrogen and at least a portion of the reaction mixture over the hydrogenation catalyst; and a weight ratio of water to glycerol in the gas phase mixture comprising glycerol and hydrogen is from about 4:1 to about 8:1

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; water is removed from the reaction mixture comprising at least one carbonyl compound prior to reacting hydrogen and at least a portion of the reaction mixture over the hydrogenation catalyst; and a partial pressure of glycerol in the gas phase mixture comprising glycerol and hydrogen is from about 40 mbar to about 400 mbar.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and water is removed from the reaction mixture comprising at least one carbonyl compound prior to reacting hydrogen and at least a portion of the reaction mixture over the hydrogenation catalyst; and the reaction stream comprising monohydric alcohol comprises less than about 10 wt. % water.

In an embodiment of the first aspect, the gas phase mixture is reacted at a temperature of from about 260° C. to about 340° C. and a pressure of about 0.5 bar to about 10 bar, and propanol makes up more than about 50% of the total mass of monohydric alcohols in the reaction stream; and water is removed from the reaction mixture comprising at least one carbonyl compound prior to reacting hydrogen and at least a portion of the reaction mixture over the hydrogenation catalyst; and the reaction stream comprising monohydric alcohol comprises less than about 5 wt. % water.

In an embodiment of the first aspect, the reaction mixture comprising at least one carbonyl compound comprises acrolein and propionaldehyde present in a weight ratio of from about 6:1 to about 0:10.

In an embodiment of the first aspect, wherein the reaction mixture comprising at least one carbonyl compound comprises acrolein and propionaldehyde present in a weight ratio of from about 1:1 to about 0:10.

In an embodiment of the first aspect, the heterogeneous catalyst system further comprises a reforming catalyst.

In an embodiment of the first aspect, the heterogeneous catalyst system further comprises a reforming catalyst, and the first reacted mixture comprises acrolein and propionaldehyde present in a weight ratio of from about 6:1 to about 0:10.

In an embodiment of the first aspect, the heterogeneous catalyst system further comprises a reforming catalyst, and the first reacted mixture comprises propanol and propionaldehyde present in a weight ratio of from about 0:10 to about 2:8.

In an embodiment of the first aspect, the heterogeneous catalyst system further comprises a reforming catalyst, the reaction mixture comprising at least one carbonyl compound comprises acrolein and propionaldehyde present in a weight ratio of from about 6:1 to about 0:10, and more than about 50% of the hydrogen is from reforming of the gas mixture.

In a second aspect, a method is provided for converting glycerol to monohydric alcohol, the method comprising reacting a gaseous mixture comprising glycerol and water in a first reaction bed comprising a heterogeneous catalyst system comprising a dehydration catalyst and a hydrogenation catalyst, whereby a first reacted mixture is produced; separating at least a portion of the first reacted mixture into a more volatile fraction and a less volatile fraction in a first condenser; reacting a mixture of hydrogen and at least a portion of the more volatile fraction from the first reacted mixture in a second reactor bed comprising a hydrogenation catalyst, whereby a second reacted mixture comprising a monohydric alcohol is produced; separating at least a portion of the second reacted mixture into a less volatile fraction comprising a monohydric alcohol and a more volatile fraction in a second condenser;

In an embodiment of the second aspect, a method is provided for converting glycerol to monohydric alcohol, the method comprising reacting a gaseous mixture comprising glycerol and water in a first reaction bed comprising a heterogeneous catalyst system comprising a dehydration catalyst and a hydrogenation catalyst, whereby a first reacted mixture is produced; separating at least a portion of the first reacted mixture into a more volatile fraction and a less volatile fraction in a first condenser; reacting a mixture of hydrogen and at least a portion of the more volatile fraction from the first reacted mixture in a second reactor bed comprising a hydrogenation catalyst, whereby a second reacted mixture comprising a monohydric alcohol is produced; separating at least a portion of the second reacted mixture into a less volatile fraction comprising a monohydric alcohol and a more volatile fraction in a second condenser; and separating at least a portion of the more volatile fraction of the second reacted mixture into a less volatile fraction comprising at least one of an aldehyde and a ketone and a more volatile fraction in a third condenser.

In an embodiment of the second aspect, at least a portion of the less volatile fraction of the first reacted mixture is introduced into the first reaction bed.

In an embodiment of the second aspect, at least a portion of the less volatile fraction of the second reacted mixture is introduced into the second reaction bed.

In an embodiment of the second aspect, at least a portion of the less volatile fraction of the first reacted mixture is introduced into the first reaction bed, and at least a portion of the less volatile fraction of the first reacted mixture is volatilized prior to introducing it into the first reaction bed.

In an embodiment of the second aspect, at least a portion of the less volatile fraction of the first reacted mixture is introduced into the first reaction bed, and at least a portion of the less volatile fraction of the first reacted mixture is volatilized prior to introducing it into the first reaction bed, and at least a portion of the less volatile fraction of the second reacted mixture is volatilized prior to introducing it into the second reaction bed.

In an embodiment of the second aspect, the gaseous mixture comprising glycerol and water further comprises hydrogen.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, and an absolute value of the heat required by the dehydration reactions is provided by an absolute value of the heat generated by the hydrogenation reactions.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, and an absolute value of the heat generated by the hydrogenation reactions provides an absolute value of the heat required by the dehydration reactions and other processes.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, and the heat required by the dehydration reactions and the heat generated by the hydrogenation reaction are balanced by controlling a ratio of an amount of dehydration catalyst to hydrogenation catalyst in the first reaction bed.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, and the heat required by the dehydration reactions and the heat generated by the hydrogenation reactions are balanced by controlling an amount of hydrogen present in the gaseous mixture.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, and the heat required by the dehydration reactions and the heat generated by the hydrogenation reactions are balanced by controlling a ratio of hydrogen to glycerol.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, the heat required by the dehydration reactions and the heat generated by the hydrogenation reactions are balanced by controlling an amount of hydrogen present in the gaseous mixture, and a molar ratio of hydrogen to glycerol in the gaseous mixture is from about 0.05:10 to about 10:10.

In an embodiment of the second aspect, the gaseous mixture comprising glycerol and water further comprises hydrogen, and the first reaction bed catalyzes dehydration reactions requiring heat and hydrogenation reactions generating heat, wherein the heat required by the dehydration reactions approximately balances the heat generated by the hydrogenation reactions, the heat required by the dehydration reactions and the heat generated by the hydrogenation reactions are balanced by controlling an amount of hydrogen present in the gaseous mixture, and a molar ratio of hydrogen to glycerol in the gaseous mixture is from about 0.1:10 to about 2:10.

In an embodiment of the second aspect, the heterogeneous catalyst system has a selectivity for conversion of glycerol to acrolein, the selectivity being greater than about 75 (wt.) %.

In an embodiment of the second aspect, the heterogeneous catalyst system has a selectivity for conversion of glycerol to acrolein, the selectivity being greater than about 85 (wt.) %.

In an embodiment of the second aspect, the heterogeneous catalyst system has a selectivity for conversion of glycerol to acrolein, the selectivity being dependent on the catalysts present, the time for the reaction, the temperature of the reaction, and the pressure of the reaction, the selectivity being greater than about 95 (wt.) %.

In an embodiment of the second aspect, the heterogeneous catalyst system has a selectivity for conversion of acrolein to propionaldehyde, the selectivity being greater than about 65 (wt.) %.

In an embodiment of the second aspect, the heterogeneous catalyst system has a selectivity for conversion of acrolein to propionaldehyde, the selectivity being greater than about 75 (wt.) %.

In an embodiment of the second aspect, the heterogeneous catalyst system has a selectivity for conversion of acrolein to propionaldehyde, the selectivity being greater than about 85 (wt.) %.

In an embodiment of the second aspect, the heterogeneous catalyst system has a selectivity for conversion of propionaldehyde to propanol, the selectivity being less than about 25 (wt.) %.

In an embodiment of the second aspect, the heterogeneous catalyst system has a selectivity for conversion of propionaldehyde to propanol, the selectivity being less than about 15 (wt.) %.

In an embodiment of the second aspect, the heterogeneous catalyst system has a selectivity for conversion of propionaldehyde to propanol, the selectivity being less than about 5 (wt.) %.

In an embodiment of the second aspect, the first reacted mixture comprising at least one carbonyl contains less than about 10 mol % of a monohydric alcohol.

In an embodiment of the second aspect, the first reacted mixture comprising at least one carbonyl contains less than about 3 mol % of a monohydric alcohol.

In an embodiment of the second aspect, the first reacted mixture comprising at least one carbonyl compound comprises monohydric alcohol and propionaldehyde present in a weight ratio of from about 0:10 to about 3:7.

In an embodiment of the second aspect, the first reacted mixture comprising at least one carbonyl compound comprises monohydric alcohol and propionaldehyde present in a weight ratio of from about 0.1:10 to about 1:9.

In an embodiment of the second aspect, the first reaction bed further comprises a reforming catalyst.

In an embodiment of the second aspect, the first reaction bed further comprises a reforming catalyst, and the first reacted mixture comprises acrolein and propionaldehyde present in a weight ratio of from about 6:1 to about 0:10.

In an embodiment of the second aspect, and the first reaction bed further comprises a reforming catalyst, the first reacted mixture comprises propanol and propionaldehyde present in a weight ratio of from about 0:10 to about 2:8.

In an embodiment of the second aspect, the first reaction bed further comprises a reforming catalyst, the first reacted mixture comprising at least one carbonyl compound comprises monohydric alcohol and propionaldehyde present in a weight ratio of from about 0:10 to about 3:7, and more than about 50% of the hydrogen is from reforming of the gas mixture.

In a third aspect, a method is provided for converting glycerol to monohydric alcohol, the method comprising contacting a gaseous material comprising glycerol with a heterogeneous dehydration catalyst at a temperature and a pressure sufficient to convert at least a portion of the glycerol to one or more compounds having at least one of a carbon-carbon double bond and a carbon-oxygen double bond, whereby a dehydrated glycerol material is obtained; adding hydrogen gas to the dehydrated glycerol material; contacting the mixture of hydrogen gas and dehydrated glycerol material with a hydrogenation catalyst at a temperature and a pressure sufficient to convert at least a portion of the compounds having at least one of a carbon-carbon double bond and a carbon-oxygen double bond to one or more monohydric alcohols, whereby a hydrogenated mixture is obtained; and separating a monohydric alcohol-rich portion from the hydrogenated mixture.

In an embodiment of the third aspect, the monohydric alcohol-rich portion comprises at least 75 wt. % monohydric alcohols.

In an embodiment of the third aspect, the monohydric alcohol-rich portion comprises at least 70 wt. % 1-propanol.

In an embodiment of the third aspect, wherein the step of contacting a gaseous material is conducted at a pressure of from about 0.5 bar (absolute) to about 10 bar (absolute), and at a temperature of from about 260° C. to about 340° C.

In an embodiment of the third aspect, the step of contacting a gaseous material is conducted at a pressure of from about 4 bar (absolute) to about 7 bar (absolute), and at a temperature of from about 280° C. to about 320° C.

In an embodiment of the third aspect, the step of contacting the mixture of hydrogen gas and dehydrated glycerol material is conducted at a pressure of from about 0.5 bar (absolute) to about 10 bar (absolute), and at a temperature of from about 150° C. to about 400° C.

In an embodiment of the third aspect, the step of contacting the mixture of hydrogen gas and dehydrated glycerol material is conducted at a pressure of from about 4 bar (absolute) to about 7 bar (absolute), and at a temperature of from about 250° C. to about 350° C.

In an embodiment of the third aspect, the dehydration catalyst comprises oxides of tungsten and zirconium.

In an embodiment of the third aspect, the hydrogenation catalyst comprises a platinum group metal.

In an embodiment of the third aspect, an amount of hydrogen in the mixture of hydrogen gas and dehydrated glycerol material is from about 0.9 to about 10 times the amount of carbon-carbon double bonds and carbon-oxygen double bonds present in the mixture on a molar basis.

In an embodiment of the third aspect, at least a portion of one compound selected from the group glycerol, propylene glycol, ethylene glycol, hydroxyacetone, propionaldehyde, acrolein, acetone, acetaldehyde, and formaldehyde is separated from the dehydrated glycerol material; and the separated portion is contacted with the heterogeneous dehydration catalyst.

In an embodiment of the third aspect, glycerol is present at a mole fraction of from about 10% to about 30%, and water is present at a mole fraction of from about 70% to about 90% in the gaseous material.

In an embodiment of the third aspect, the gaseous material further comprises at least one monohydric alcohol.

In an embodiment of the third aspect, the gaseous material further comprises at least one monohydric alcohol, and the monohydric alcohol is selected from the group consisting of methanol, ethanol, and propanol.

In an embodiment of the third aspect, the gaseous material further comprises at least one monohydric alcohol, and monohydric alcohols make up from about 0.1 wt. % to about 30 wt. % of the gaseous material.

In an embodiment of the third aspect, the gaseous material further comprises at least one monohydric alcohol, and monohydric alcohols make up from about 0.1 wt. % to about 15 wt. % of the gaseous material.

In an embodiment of the third aspect, the gaseous material further comprises at least one monohydric alcohol, and monohydric alcohols make up from about 0.1 wt. % to about 5 wt. % of the gaseous material.

In an embodiment of the third aspect, the gaseous material further comprises at least one monohydric alcohol, and monohydric alcohols make up from about 0.1 wt. % to about 2 wt. % of the gaseous material.

In an embodiment of the third aspect, the gaseous material further comprises at least one monohydric alcohol, and monohydric alcohols make up less than about 0.5 wt. % of the gaseous material.

In an embodiment of the third aspect, the gaseous material further comprises at least one fatty acid methyl ester.

In an embodiment of the third aspect, the gaseous material further comprises at least one fatty acid methyl ester, and fatty acid methyl esters make up from about 0.1 wt. % to about 2 wt. % of the gaseous material.

In an embodiment of the third aspect, the gaseous material further comprises at least one fatty acid ethyl ester.

In an embodiment of the third aspect, the gaseous material further comprises at least one fatty acid ethyl ester, and fatty acid ethyl esters make up from about 0.1 wt. % to about 2 wt. % of the gaseous material.

In an embodiment of the third aspect, the gaseous material further comprises at least one fatty acid propyl ester.

In an embodiment of the third aspect, the gaseous material further comprises at least one fatty acid propyl ester, and fatty acid propyl esters make up from about 0.1 wt. % to about 2 wt. % of the gaseous material.

In an embodiment of the third aspect, the gaseous material contains from about 0.1 wt. % to about 20 wt. % hydrogen.

In an embodiment of the third aspect, the gaseous material further comprises hydrogen at about 0.2% to about 2% (molar).

In a fourth aspect, a method is provided for converting glycerol to monohydric alcohol, the method comprising contacting a gaseous material comprising glycerol with a heterogeneous dehydration catalyst at a temperature and a pressure sufficient to yield a first reacted material comprising carbon monoxide, water, and one or more carbonyl-containing molecules; contacting the first reacted material with a water-gas shift reaction catalyst at a temperature and a pressure sufficient to yield a second reacted material comprising hydrogen; and contacting the second reacted material with a heterogeneous hydrogenation catalyst at a temperature and a pressure sufficient to convert at least a portion of the carbonyl-containing molecules to one or more monohydric alcohols in a hydrogenated material.

In an embodiment of the fourth aspect, the step of contacting a gaseous mixture occurs at a temperature of from about 250° C. to about 380° C., and at a pressure of from about 1 bar (absolute) to about 10 bar (absolute).

In an embodiment of the fourth aspect, the step of contacting a gaseous mixture occurs at a temperature of from about 280° C. to about 320° C., and a pressure of from about 4 bar (absolute) to about 7 bar (absolute).

In an embodiment of the fourth aspect, the heterogeneous dehydration catalyst comprises oxides of tungsten and oxides of zirconium.

In an embodiment of the fourth aspect, the step of contacting the first reacted material is conducted at a temperature of from about 220° C. to about 380° C., and at a pressure of from about 1 bar (absolute) to about 10 bar (absolute).

In an embodiment of the fourth aspect, the step of contacting the first reacted material is conducted at a temperature of from about 270° C. to about 330° C., and at a pressure of from about 4 (absolute) to about 7 bar (absolute).

In an embodiment of the fourth aspect, the contacting with a heterogeneous hydrogenation catalyst occurs at a temperature of about 150° C. to about 400° C., and the pressure of about 0.5 to about 10 bar (absolute).

In an embodiment of the fourth aspect, the step of contacting the second reacted material is conducted at a temperature of from about 250° C. to about 350° C., and at a pressure of from about 4 bar (absolute) to about 7 bar (absolute).

In an embodiment of the fourth aspect, an alcohol-rich material and an alcohol-depleted material are separated from the hydrogenated material, and the alcohol-depleted material comprises predominantly carbon dioxide and hydrogen.

In an embodiment of the fourth aspect, an alcohol-rich material and an alcohol-depleted material are separated from the hydrogenated material; the alcohol-depleted material comprises predominantly carbon dioxide and hydrogen, and the alcohol rich material comprises at least 70 wt. % 1-propanol.

In an embodiment of the fourth aspect, an alcohol-rich material and an alcohol-depleted material are separated from the hydrogenated material, and the alcohol-depleted material comprises predominantly carbon dioxide and hydrogen; the alcohol-depleted material is treated via pressure-swing absorption to remove at least a portion of the carbon dioxide present, resulting in a carbon dioxide-rich material and a hydrogen-rich material; and the hydrogen-rich material is recycled to the step of contacting a gaseous material.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Conversion of Glycerol to Monohydric Alcohols

A process for converting glycerol as a byproduct of biodiesel production into more useful monohydric alcohols is provided. The process involves two reaction steps. In the first step, glycerol or other polyhydric alcohol(s) present in a biodiesel byproduct stream are dehydrated over a solid catalyst to yield acrolein and other dehydrated products.

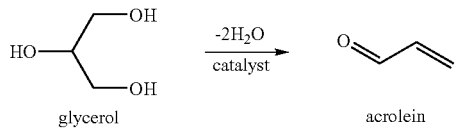

In a second step, the dehydrated products are hydrogenated to yield, e.g., high value products including monohydric alcohols.

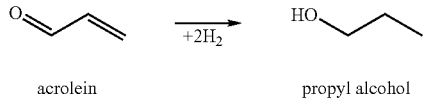

Under some reaction conditions, other intermediates can be produced, including glycols. The 3-carbon chain of the glycerol can also be cleaved under certain reaction conditions, as discussed in detail below. Such intermediate cleavage products can include lower aldehydes. These intermediates can be further reacted to corresponding monohydric alcohols.

Figure 1:
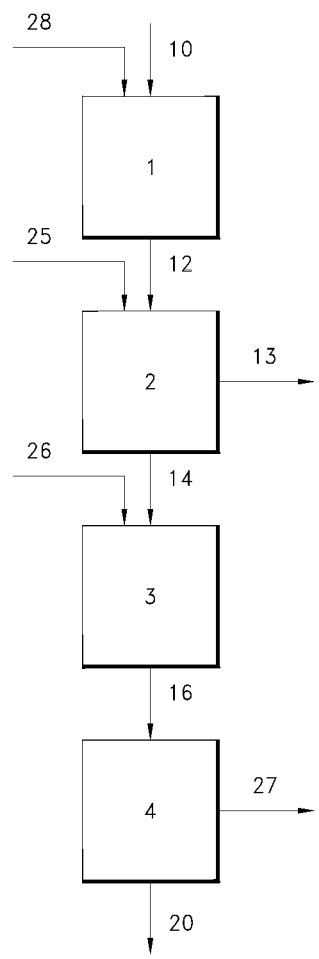
FIG. 1 is a block diagram of a process for converting glycerol to monohydric alcohols.

A process for producing monohydric alcohols from glycerol according to a preferred embodiment, which can be integrated into a biodiesel production process, is depicted schematically in FIG. 1. A polyhydric alcohol feed 10 is subjected to dehydration conditions 1. The product stream 12, including acrolein and other dehydrated products, is then subject to a separation step 2, whereby acrolein and aldehydes in gaseous form 14 are separated from less volatile components such as water. The gaseous stream 14 is then subjected to hydrogenation conditions 3. Hydrogen 25 can be added to the gaseous products 14 prior to or at the separation step 2 and/or at the hydrogenation step 3 (as hydrogen 26). The resulting hydrogenated products 16 are subjected to a further separation step 4, whereby a stream rich in monohydric alcohols 20 is separated from another material that can contain unreacted glycerol and hydrogen and intermediates such as aldehydes, acrolein, hydroxy acetone, and the like. Although not depicted in FIG. 1, other separation and reaction steps can be employed in the process, as can the recycle of unreacted or only partially reacted species, and the use of multistage operations for one or more of these steps, as are appreciated by one of skill in the art, and as is discussed in detail elsewhere herein.

Polyhydric Alcohol Feedstream

As discussed above, the methods and apparatus of preferred embodiments are useful in converting glycerol as a byproduct in biodiesel production into higher value monohydric alcohols. Accordingly, a glycerol byproduct stream from biodiesel production is a particularly preferred feedstream; however, any other suitable feedstream containing polyhydric alcohols can be subjected to the process as described herein to yield higher value monohydric alcohols. Examples of other such feedstreams include, but are not limited to, feedstreams from fat-splitting and transesterification processes as well as streams that include glycerol from some other source, or glycols such as propylene glycol, ethylene glycol.

The glycerol byproduct stream generated in biodiesel production frequently includes glycerol, methanol, catalyst(s), and other compounds. If a different alcohol is used in the biodiesel production instead of or in addition to methanol, this alcohol could be present in the byproduct stream instead of or in addition to the methanol. The glycerol byproduct stream can be refined and purified, resulting in a primarily glycerol/water mixture containing from about 20 to about 40 wt. % glycerol. However, the particular methods and operating conditions employed can affect concentrations and compositions such that the relative amounts may vary. While a feedstream containing essentially glycerol (about 100 wt. %) is particularly preferred, polyhydric alcohols, more generally (for example, propylene glycol, ethylene glycol, glycerol, etc.) and combinations of polyhydric alcohols are also acceptable. Feedstreams containing water and other impurities in combination with polyhydric alcohols can be processed, although for product purification purposes, it is generally preferred that the feedstream be anhydrous or contain only a minimal amount of water. Typical polyhydric alcohol contents of feedstreams amenable to the processes of preferred embodiments are preferably at least about 5% or higher, more preferably 10% or higher, and more preferably 20% or higher, 30% or higher, 40% or higher, 50% or higher, 60% or higher, 70% or higher, 80% or higher, or most preferably 90 wt. % or higher.

While complicating purification, the presence of water can provide some benefits. For example, it can act as a heat sink during processing which can moderate the reaction rates, it can facilitate reaction control, and it can facilitate broader reaction temperatures. Accordingly, in certain embodiments it can be desirable to have a water concentration in the feedstream of preferably 95% or lower, more preferably 90% or lower, 80% or lower, 70% or lower, 60% or lower, 50% or lower, 40% or lower, 30% or lower, 20% or lower, or about 10% or lower by weight.

Other impurities that can be present in typical glycerol and polyhydric alcohol feedstreams include triacyl glycerides, partial glycerides, phospholipids, lysophospholipids, free fatty acids, soaps, sterols, salts, and the like. While it is generally preferred to minimize the amount of such impurities in the feedstream, the presence of a small amount of these impurities is generally tolerable and will not significantly impact the production of monohydric alcohols.

It is generally preferred to minimize the salt content of the feedstream. Preferred feeds have an ash value of approximately 2% or less, based on AOCS Test Method Ea 2-38 (American Oil Chemists' Society). Other feed materials acceptable for use can have approximately 4-5% ash and others may have as much as 8% or 10% ash content or higher. The ash content can be due to residual catalyst from the production of biodiesel, to minerals present in the water used for processing biodiesel, or to some other source such as carryover with the feed oil, or the like.

Phosphorus contaminants may also be present, such as from phospholipids or lysophospholipids present in the feed oil or residual phosphate/phosphoric acid from processing. While it is desirable to minimize phosphate content, phosphate concentrations in the feed of less than about 5 ppm can be acceptable, and concentrations of about 5-100 ppm or even higher can be tolerable.

Generally, contaminants such as phospholipids and salts, or volatile contaminants with vapor pressures lower than glycerol do not present issues for the processes of preferred embodiments, as they can be substantially removed by vaporizing the feedstream. In some instances, careful selection of the vaporization conditions, such as temperature, pressure, water content, gas flow, and the like can enable the concentration of contaminants in the gas phase to be minimized. Such selections can be readily made by one of skill in the art after examination of the vapor pressure characteristics of the feed material components.

In certain embodiments, it can be desirable to further refine the feed material, such as when the contaminants have an adverse effect on catalyst life, activity or selectivity. Suitable refining methods include, but are not limited to distillation, filtration, absorption, and adsorption methods.

Other contaminants include monohydric alcohols, such as are leftover from transesterification operations, and hexane, heptane, and other solvent remaining after oil crushing operations. These contaminants can be removed, if desired, by e.g. volatilizing prior to vaporization of the glycerol in a flash tank, evaporator, still, or the like. However, in certain embodiments it can be acceptable for the contaminants to remain in the feed material and be removed in a downstream operation. Alcohol may also be present due to recycling/utilization of downstream materials.

The feedstream can be in any suitable state, such as gaseous, liquid, and/or vapor; however, it is generally preferred to use a gaseous feedstream (or to convert a liquid or vapor feedstream to a gaseous feedstream via heating or reduction of pressure) as a feed to the gas phase dehydration step.

Dehydration of Polyhydric Alcohols

The first step in the glycerol or polyhydric alcohol conversion process is typically a gas phase dehydration step over a suitable heterogeneous catalyst. The dehydration reaction converts the glycerol, glycols, and other (poly)ols present in the feedstream primarily to acrolein, hydroxy acetone, aldehydes and alcohols. Suitable catalysts include those known in the art for gas phase dehydration processes, including acids (e.g., supported phosphoric or sulfuric acid), H-mordenite, Ce-mordenite, zeolite 13X, $NH_4^+$ exchanged zeolite 13X, oxides of titanium, zirconium, hafnium, silicon, germanium, tin, cerium, thorium, aluminum, chromium, zinc, and tungsten as well as such oxides modified with an alkali metal or alkaline earth metal and/or an acidic material. Suitable catalysts can also include combinations of these individual catalysts, for example, tungsten and cerium oxides ($WO_3/CeO_2$), tungsten and zirconium oxides ($WO_3/ZrO_2$), tungsten and titanium oxides ($WO_3/TiO_2$), and tungsten oxides with mordenite ($WO_3$/mordenite). The catalyst can be supported on a suitable support such as a zeolite, alumina, kiselgur and/or silica; however, unsupported catalysts can also be desirable in certain applications. The active part of the catalyst is typically only a portion of the catalytic particle, such as with 10% $WO_3/TiO_2$, 10% $WO_3/CeO_2$, 10% $WO_3/ZrO_2$, 25% (wt.) $H_3PO_4$/spinel, and 25% (wt.) $H_3PO_4$/alumina A particularly preferred reactor for use in the dehydration step is a plug flow reactor (PFR) or tubular reactor with a fixed catalyst bed; however, any suitable reactor for use in dehydration can be employed. While continuous flow reactors are particularly preferred due to ease of process integration, batch reactor configurations can also be employed.

The feedstream is preferably introduced into the dehydration reactor as a gas. If a liquid feedstream is employed, then it can be converted to a gas by conventional methods, such as by heating or a reduction in pressure. The extent of reaction typically depends upon the specific type and amount of catalyst, the feedstream composition, the temperature, the pressure, the gas velocity, the degree of mixing, and the reactor space time; however, it is generally preferred to operate the reactor at a temperature of from about 220° C. to about 340° C., more preferably from about 250° C. to about 310° C., a total pressure of from about 0.1 bar to about 10 bar (absolute), more preferably from about 1 to about 7 bar (absolute), and most preferably from about 1 to about 5 bar (absolute), and with a feed composition of from about 5 to about 50 wt. % glycerol and from about 95% to about 50 wt. % water. In certain embodiments, the reaction can be operated under different conditions, such as at a temperature as low as about 200° C. or lower or as high as about 400° C. or higher. Under very low pressures (0.1 bar or lower), the reduced boiling points of glycerol and water can allow operation of the reactor at lower temperatures (about 200° C. or lower). Similarly, low or reduced concentrations of glycerol can allow operation of the reactor at lower temperatures (about 200° C. or lower), as the partial pressure of glycerol can still be kept below the saturation pressure of glycerol at the operating temperature. Higher temperature and/or lower pressure can allow operation of the reaction at higher glycerol concentrations. Other conditions may be acceptable in certain embodiments, such as when a particular final alcohol composition is desired. For example, higher pressures favor propanol and lower pressures favor a mixture of $C_1$-$C_3$ monohydric alcohols (such as propanol, ethanol, and methanol). The reaction mixture can be heated or cooled to control the reaction as it progresses through the catalyst, such as by using heating or cooling jackets or coils, electrical heaters, or by introduction of one or more other gases of the same or a different temperature.

Separation of Dehydrated Intermediates

The product stream 12 from the dehydration reactor is preferably subjected to a separation step to remove components such as water and various side reaction products from the desired intermediates to yield a product stream rich in aldehydes, acrolein, and monohydric alcohols. The separator is preferably a condenser that condenses the water and other high boiling components, thereby removing them from the gaseous product stream. While use of a condenser in the separation step is particularly preferred, other processes as known in the art for removing undesired components of the product stream can also be employed, such as distillation, solvent separation, adsorbents, reactive chemicals, and the like.

When a condensation process is employed, the separation can be performed in a single condenser, or in multiple condensers optionally operating at different temperatures and/or pressures. In a preferred embodiment, the inlet stream is cooled when it enters the separating chamber, resulting in partial condensation of the inlet stream. The condensed material is then directed from the chamber as a separate stream from the remaining gaseous material. In other embodiments, the inlet stream is cooled prior to entering the separation chamber, or the inlet stream is compressed to a higher pressure prior to entering the separation chamber, the higher pressure resulting in partial condensation of the inlet stream. Alternatively, the inlet stream can be heated prior to compression to reduce condensation of the compressed stream, either in the vicinity of the compressor or prior to cooling to control the location at which condensation occurs.

In certain embodiments, a distillation apparatus separates the desired dehydrated intermediates from water and other impurities. Any suitable distillation apparatus can be employed, for example, a packed column or a tray column. The inlet stream can be a gas stream or a fully condensed stream, or a partially condensed stream, and interchange of chemical species occurs between the rising gas phase and a falling liquid stream of condensed material.

In other embodiments, while it is generally desirable to minimize these components, however, in certain embodiments it may be desirable to introduce a noncondensable gas into the feed to the separation device or into the separation device itself to assist in the separation of the desirable intermediates and final products. Suitable gases include inert gases such as helium, argon, nitrogen, air, other gases including reactive gases such as hydrogen, carbon monoxide, carbon dioxide, and hydrocarbons and mixtures thereof.

The temperature and pressure at which the separator is operated, as well as the type of separator employed, impact the efficiency and product distribution characteristic of the separation that occurs. Preferred temperatures and pressures can be selected based on the composition of the inlet stream. The operating conditions are typically selected so as to provide a low level of losses of desirable intermediates and final products to the waste stream and a low level of water and side products in the gas stream subjected to further processing in, for example, the hydrogenation step. Although the presence of water in the hydrogenation step usually does not present issues, it may be more difficult to separate the water at a later process step; accordingly, it is generally preferred to minimize the amount of water present in the hydrogenation step. Separation conditions can generally be selected based on the composition of the feed and the vapor pressure characteristics of the feed components and mixtures thereof. Water separation techniques or devices can optionally be used as a part of the separation step. Such water separation methods include membrane techniques, adsorption techniques, desiccants, etc.

Hydrogenation of Intermediates to Yield Monohydric Alcohols

The second reaction step in the process of the preferred embodiments is a hydrogenation step. The intermediates product stream 14 from separation step 2 is mixed with hydrogen gas in a second reactor under suitable process conditions, resulting in hydrogenation of unsaturated components in the intermediates product stream. Preferred hydrogenation catalysts include those based on the platinum group metals (platinum, palladium, rhodium, ruthenium, osmium, iridium), nickel, and copper. The catalyst may be supported or unsupported. Suitable supports include alumina, silica, carbon, spinel, and other such materials. Suitable hydrogenation catalysts are manufactured by BASF Catalysts (Iselin, N.J.), Johnson Matthey (London, England), Sud-Chemie (Munich, Germany), Topsoe (Lyngby, Denmark) and others. The primary hydrogenation reactions result in the saturation of the carbon-carbon double bond of acrolein and reduce carbonyl groups present in aldehydes and acrolein to hydroxyl groups, yielding monohydric alcohols.

The hydrogen employed in the hydrogenation step can be added directly to the hydrogenation reactor with the intermediates process stream, or at least a portion of the hydrogen can be added to the intermediates process stream at any other suitable point upstream, such as before, during, or after the first separation step. Hydrogen in limited quantities can also be added with the initial feed. Alternatively, the hydrogen can be added in portions to a hydrogenation reactor with reaction taking place between hydrogen additions. Batch reactors can be advantageously employed; however, continuous flow reactors such as tubular or plug flow reactors are typically preferred. The hydrogenation reactor can optionally include one or more intermediate heaters, coolers, compressors, and combinations thereof. The reactor temperature is typically from about 200° C. to about 290° C., but temperatures as low as about 150° C. or less, or as high as about 400° C. or more may be used. The reactor pressure can be from about 0.1 bar (absolute) to about 10 bar (absolute), more preferably from about 0.5 bar (absolute) to about 7 bar (absolute), and most preferably from about 1 bar to about 5 bar (absolute). The amount of hydrogen can be up to about two times stoichiometric. However, higher levels such as up to about 10 times stoichiometric can be advantageously employed, especially when provision is made to recycle or recover the excess hydrogen.

In preferred embodiments, at least a portion of the heat generated in the hydrogenation reaction is removed by heat transfer to cooling jackets or cooling coils. Alternatively, at least a portion of the heat of reaction can be removed by heat transfer to the surrounding environment. In other embodiments, the reaction proceeds in a sequence of stages with cooling devices or heat exchangers between at least two of the stages. Alternatively, the reaction rate can be controlled by addition of hydrogen in stages, or by selecting an amount of cooling area associated with a reactor.

Purification of Monohydric Alcohols

The second separation step 4 in the process shown in FIG. 1 is a partial condensation or a step-wise condensation of the components of the outlet stream from the hydrogenation reaction. For example, the stream can be cooled to a temperature below the boiling point of the monohydric alcohols present. For methanol (boiling point 64.7° C. at 1 atmosphere), a temperature of about 60° C. at a pressure of about 1 atmosphere can be desirably employed, with the resulting condensate removed. Alternatively, the stream can be cooled step-wise, first to about 140° C. at about 1 atmosphere (below the boiling point of hydroxyacetone) to condense glycerol, glycols and hydroxyacetone that may be present, and then to about 60° C. at about 1 atmosphere to condense monohydric alcohols that may be present, with removal of the resulting condensate at each step. In another embodiment, the first condensation step occurs at a temperature sufficiently high to remain above the boiling point of hydroxyacetone, such as from about 150° C. to about 185° C. at about 1 atmosphere and the second condensation step occurs at a temperature below the boiling point of any monohydric alcohols that are present.

In another embodiment, the outlet stream from the hydrogenation reaction can be cooled first to condense the polyhydric alcohols at a temperature of from about 150° C. to about 185° C. at about 1 atmosphere, then cooled to condense hydroxyacetone at a temperature of from about 100° C. to about 143° C. at about 1 atmosphere, then further cooled to a temperature of from about 58° C. to about 63° C. to condense monohydric alcohols with the resulting condensate removed at each stage. In certain embodiments, a fourth cooling step to condense and remove carbonyl-containing compounds by cooling to below the boiling point of the specific compound (for example, acetone at 56.5° C., acrolein at 53° C., propionaldehyde at 46-50° C., acetaldehyde at 20.2° C., and formaldehyde at −19.3° C.).

The temperatures described above for the condensation stages are for operation at about 1 atmosphere. The specific temperatures selected can readily be adjusted for different operating pressures based on the changes in the boiling points of the specific compounds present, with higher temperatures generally used at higher pressures and lower temperatures at lower pressures.

In certain embodiments, distillation equipment can be used with or in place of the condensation/separation steps. The operating conditions for such distillation equipment are selected based on the boiling points of the various compounds present at the operating pressures.

Preferably, at least two condensation stages are employed with the outlet stream from the hydrogenation step. The stream is first cooled to condense glycols that are present, such that they are separated from gas phase monohydric alcohols. Preferably, at least about 50 wt. % of the glycols are condensed in the first condensation step, and this stream may contain hydroxyacetone. This step can be followed by condensation of the monohydric alcohols present. Preferably, at least about 50 wt. % of the monohydric alcohols are condensed in the second condensation step. A subsequent condensation step can be employed to separate aldehydes and ketones present. However, in certain embodiments, these aldehydes and ketones can be condensed with the monohydric alcohols or they can remain with the noncondensed stream or they can be divided with a portion remaining with the noncondensed stream and a portion condensing with the monohydric alcohols. When the aldehydes and ketones are condensed in a separate stage, preferably at least about 50 wt. % of the aldehydes and ketones present are condensed in the subsequent condensation step. The specific temperature of each step can be selected based on the operating pressure and the boiling point of the compounds present. The glycerol containing stream is preferably recycled to the dehydration reactor, and the aldehydes and ketones are preferably recycled to the hydrogenation reactor. When condensed in a separate stage, hydroxyacetone is preferably recycled to the hydrogenation stage.

Cooling for the condensation steps can be achieved by any suitable method, such as the use of at least one heat exchanger, or through at least one wall of the separator vessel. Alternatively, at least one distillation column can be used to perform at least one separation of the product stream (or a fraction thereof) of the hydrogenation reaction. In other embodiments, at least one compressor is used in place of or in addition to at least one cooler (for example, a heat exchanger). While condensers and distillation columns are particularly preferred separators, other separation devices can also be employed, as are known in the art (for example, stills, cyclones, membranes, and the like, and those based on absorption and adsorption principles).

Recycle Streams

The process can be operated in a "once-through" fashion, with no recycle of separated materials. However, in certain embodiments it can be desirable to collect streams of separated materials or other materials from different points in the process, either for recycle to different points in the process of the preferred embodiments, as feedstock in other processes, for further separation or fractionation on other equipment, for storage, and/or for use as a final product. For example, an effluent stream from the second separation step 4 can be recycled to the first separator 2. The recycled stream can be a gas stream, and can optionally contain (or consist only of) hydrogen gas. In another embodiment, an effluent stream from the second separation step 4 is recycled to the first reaction step 1; for example, a recycle stream including one or more glycols is recycled to the first reaction step 1. In yet another embodiment, an effluent stream from the second separation step is recycled to the second reaction step 3, for example, a recycle stream including hydroxyacetone.

Monohydric Alcohol Product Stream

The product stream composition can vary depending on a variety of factors, including how the second separation step is operated. For example, in one embodiment, only the residual gases noncondensible at atmospheric pressure and normal room temperature are removed. In this particular embodiment, the composition of the product stream can include monohydric alcohols and incompletely reacted feed and intermediates. The incompletely reacted materials can include, depending on the extent of the reactions, at least one of glycerol, glycols, aldehydes, and hydroxyacetone. Such mixed product streams can be useful in certain applications, or can be useful for further processing at a different time or location to yield valuable products or intermediates.

Alternatively, the second separation step can separate the noncondensible gases and one or more condensed liquid streams from the product stream. The composition of the streams can depend on the operation of the second separation step, but generally, for the noncondensible gas stream as described above, the condensed liquid stream composition typically contains at least one of glycols and glycerols. The product stream can also include monohydric alcohols, which are generally the most desirable products of the process. Other intermediate products, such as aldehydes and hydroxyacetone can be present in the product stream, the condensed liquid stream, or both streams. Further, the aldehydes and hydroxyacetone can be present together in one stream or separated between the streams, depending on the operation of the second separation step. The condensed liquid stream can be stored, used in certain applications, re-introduced into the process at a different times and/or locations, or recycled. In certain embodiments, the condensed liquid stream is recycled to the first reaction step. The product stream can be used for a desired purpose, or stored.

In certain embodiments, the second separation step separates the noncondensible gases and two condensable liquid streams from the product stream. The noncondensible gas stream is typically as described above. The two condensed liquid streams can be characterized as one rich in glycols and possibly glycerol with the other rich in hydroxyacetone. The product streams are rich in monohydric alcohols. The condensed liquid streams can be recycled to the process at, for example, the first reaction step and/or the second reaction step, or they can be collected for other uses or processed at a later time or place.

The actual composition of the product stream when two other condensed liquid streams are to be produced therefrom preferably has a composition that depends upon the operation of the overall system. For example, a typical composition is desirably about 90% or more by weight monohydric alcohol with hydroxyacetone, propionaldehyde and other carbonyl-compounds as possible contaminants. If the operation of the second separation step is changed such that a lower temperature is employed for the hydroxyacetone separation, less hydroxyacetone is likely to be in the product stream, but additional losses of alcohol are possible. If the temperature is increased, however, the amount of hydroxyacetone in the product stream may increase. Alternatively, changes to the hydrogenation conditions can result in more aldehydes/ketones present in the product stream.

Process Modifications—Combined Dehydration and Hydrogenation

In another embodiment, the first reaction step can optionally involve a combination of dehydration and hydrogenation reactions. An additional hydrogenation step can be performed downstream of this reaction step. At least a portion of the hydrogen used in the process can be added at the first reaction step, as illustrated in FIG. 1 with hydrogen stream 28, to, for example, improve the conversion of at least a portion of the polyhydric alcohol to monohydric alcohol. For conversion of glycerol to 1-propanol, the reaction equations are:

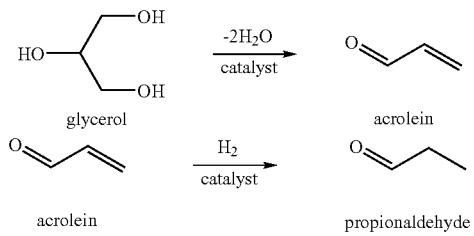

The propionaldehyde can then be converted to propanol in this reaction step or in another.

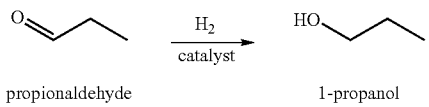

Other alcohols or alcohol mixtures can be produced by varying the material fed to the reactor and/or changing the reaction conditions. For example, propylene glycol or ethylene glycol may be fed. Also, the reaction pressure can be varied, with higher pressures, for example, favoring conversions of glycerol to 1-propanol and lower pressures favoring conversion of glycerol to a mixture of ethanol, methanol, and propanol with the first reaction step converting the glycerol to the corresponding aldehyde or mixture of aldehydes.

Reactor 1 can include a mixed bed of hydrogenation and dehydration catalysts. Reactor 1 can also include a bed of dehydration catalyst(s) in series with a mixed bed of hydrogenation catalyst(s). Preferred hydrogenation and dehydration catalysts include those described above. In one embodiment, a mixed bed of approximately 90 wt. % dehydration catalyst and 10 wt. % hydrogenation catalyst is employed. In another embodiment, from about 10% to about 35 wt. %, or from about 35 wt. % to about 55 wt. % of the mixed bed is hydrogenation catalyst. In yet other embodiments, up to about 90 wt. % of the mixed bed is hydrogenation catalyst. In embodiments wherein there is both a dehydration bed and a mixed bed, these beds can be enclosed in separate reactor housings, or they can be in a common housing. In further embodiments, there can be more than one bed of a given type or there can be more than one bed of each.

When a mixed catalyst bed is employed, with or without a dehydration catalyst bed, it is typically preferred to feed at least a portion of the hydrogen gas to reactor 1, typically a sub-stoichiometric quantity of hydrogen based on complete conversion of glycerol to 1-propanol. The amount of hydrogen fed is typically from about 40% to about 500% of the stoichiometric amount, but in some instances it can advantageously be from as low as 10% or less to about 10,000% or more of stoichiometric.

In a preferred embodiment, an amount of hydrogen is employed in the first reaction step to achieve a high degree of conversion to propionaldehyde with a low degree of conversion to alcohol. For example, acrolein and propionaldehyde can be present in a weight ratio of from about 6:1 to about 0:10, or from about 1:1 to about 0:10, or even from about 3:7 to about 0:10, or from about 1.5:8.5 to about 0:10, or from about 0.1:10 to about 1:9. The amount of hydrogen that reacts in this embodiment is typically about 1 mole per mole of glycerol; however, due to the reversible nature of the reaction and the possibility of further reaction to alcohol, an amount somewhat in excess of about a 1:1 molar ratio and below about a 1:2 molar ratio is generally be preferred.

Reducing the amount of acrolein in the product stream offers benefits related to safety and ease of separation of water from the reaction mixture. When no hydrogenation takes place due to no hydrogenation catalyst or no hydrogen, one of the primary reaction products is acrolein. Acrolein is generally an undesirable intermediate due to its instability, toxicity, and carcinogenicity. For safety reasons, it is desired to maintain a relatively low concentration of acrolein in the system, and not conduct steps that result in its concentration.

If the water is not removed after the first reaction step, it is instead removed later in the process, such as after the hydrogenation step has converted intermediates to alcohols. Removal of the water at this later point in the process can be significantly more difficult due to the presence of compounds such as 1-propanol and ethanol which can form azeotropes with water and/or have boiling points significantly closer to that of water and the intermediate acrolein. For example, the boiling point (at 1 atmosphere) of acrolein is 52.5° C., the boiling point of 1-propanol is 97.2° C., the boiling point of ethanol is 78.5° C., and the boiling point of propionaldehyde is 48.8° C.

Conversion of at least a portion of the acrolein to propionaldehyde in the first reaction step can desirably reduce the concentration of acrolein within the system generally, and also can facilitate the separation of water by allowing the water to be separated from a stream comprising propionaldehyde, such as stream 12, which has a relatively lower boiling point, instead of 1-propanol, which has a relatively high boiling point, or acrolein. Separation of water from propionaldehyde rather than from 1-propanol has the further advantage of the propionaldehyde-water azeotrope having a water content of only about 2 wt. % instead of about 28 wt. % for 1-propanol at 1 atmosphere. One of the myriad advantages of the combined reactor configuration is that it supports the isolation and removal of water prior to conversion of intermediates into monohydric alcohol, which in turn reduces the complexity of achieving a high quality monohydric alcohol product stream with little water present.

In a preferred embodiment of the mixed bed of hydrogenation and dehydration catalysts, sufficient hydrogen is added to the first reaction step to balance the heat requirements of the endothermic dehydration with the heat generation of the exothermic hydrogenation. The amount of hydrogen reacted to approximately balance the heat requirements will depend on the degree of conversion of the glycerol to various compounds at this point in the process, such as acrolein, propionaldehyde, propanol, formaldehyde, acetone, propanol, methanol, ethanol, and hydroxy acetone. The amount of heat lost through the reactor walls as well as any desired temperature rise or fall across the reactor can also be considered in balancing the heat required for endothermic dehydration with the exothermic hydrogenation. In some embodiments, the amount of hydrogen reacted to approximately balance the heat requirements can be about two-thirds to about three-fourths of a mole of hydrogen per mole of glycerol. In other embodiments, the amount of hydrogen reacted can be about 0.03 to about 0.7 mole of hydrogen per mole of glycerol or about 0.06 to about 0.5 mole of hydrogen per mole of glycerol, or even about 0.1 to about 0.3 mol of hydrogen per mole of glycerol. As discussed above, the actual amount of hydrogen is preferably slightly in excess of this amount. At least partial balancing of the heat requirements for these reactions can improve the energy efficiency through direct utilization of the heat generated during hydrogenation. The heat from the exothermic hydrogenation can also be collected, such as with heat exchangers, and used at other points within the process or for other uses entirely such as a heat source for the production plant, or the nearby locale.

In certain embodiments, the amount of hydrogen added to the first reaction step can be adjusted based on various measurements such as the relative flow rates of glycerol and hydrogen, the outlet temperature of the reactor bed, comparison of the inlet and outlet temperature of the reactor bed, analysis of the reactor bed outlet stream composition, etc.

Alternatively, similar results can be achieved by using more hydrogen but limiting the amount of catalyst, thereby effectively limiting the extent of hydrogenation that occurs at the first reaction step. Similarly, the different catalysts present within the combined bed can be distributed so as to support proper thermal energy transfer and management of the reactions taking place.

Single Reaction Step

Figure 2:
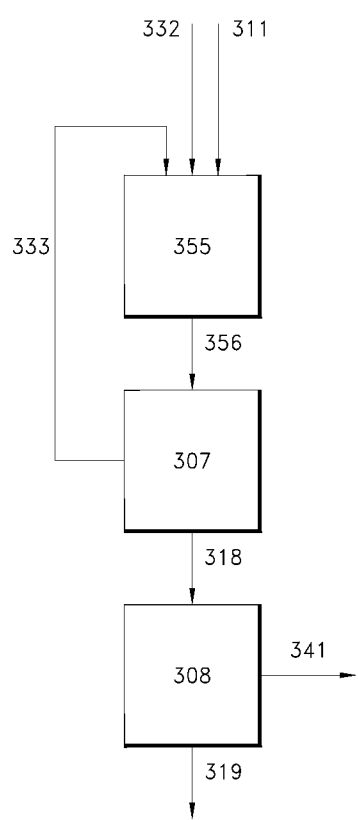
FIG. 2 is a schematic diagram of a process for converting glycerol to monohydric alcohols with a combined dehydration-hydrogenation reaction step.

In another embodiment, as depicted in the scheme of FIG. 2, all of the dehydration and hydrogenation takes place in a single reaction step, followed by separation steps to remove excess hydrogen and water. The reaction step in this embodiment includes one or more reactor beds with dehydration and hydrogenation catalysts for gas phase conversion of polyhydric alcohols to monohydric alcohols. The conversion of glycerol to 1-propanol is accomplished according to the following net reaction:

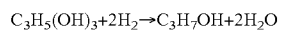

$$C_3H_5(OH)_3 + 2H_2 \rightarrow C_3H_7OH + 2H_2O$$

Different reaction conditions can lead to different products. For example, lower reactor pressures favor a mixture of alcohols.

FIG. 2 schematically shows an embodiment of such a process wherein the glycerol conversion occurs in reactor 355. In this embodiment, the feedstream comprising glycerol and water is fed to reactor 355. Hydrogen gas 332 is mixed with the glycerol feedstream in reactor 355 or before the reactor. The gaseous feedstream with hydrogen contacts catalyst in reactor 355 at about 300° C. Suitable catalysts are those that can support a multistep reaction, such as a mixture of dehydration catalyst and hydrogenation catalyst as previously described. The reaction can take place in two steps where the first step involves dehydration (removal of water) of the glycerol. Suitable catalysts for dehydration reactions include acidic materials such as mineral acids, and phosphoric acid on various solid supports such as alumina or silica. Other acidic materials include solid acids such as y-alumina, aluminum silicates, zeolites, and the like. In the second step, the dehydrated product is hydrogenated (hydrogen addition). Suitable hydrogenation catalysts include nickel and precious metals such as nickel, copper, and platinum group metals (platinum, palladium, rhodium, ruthenium, osmium, iridium, and the like). These two reaction steps are preferably combined, as with a mixed catalyst bed, but in some instances separate reaction beds for each catalyst or a mixed catalyst bed and a bed with a single catalyst can be used together in a single reactor. In some embodiments, a reactor bed can be a reactive distillation column in which intermediate products are condensed and recycled back to the hot inlet stage where they are vaporized again and mixed with feedstream 311 or added directly to reactor 355 and flow in contact with the catalyst. The propanol, water and hydrogen mixture 356 passes out of reactor 355 to a condensing separator 307 in which unreacted hydrogen 333 is isolated, and optionally returned to reactor 355. The liquid propanol and water mixture 318 passes to the water removal module 308 in which the propanol is dried into a usable alcohol stream 319 and byproduct water stream 341.

Figure 2A:
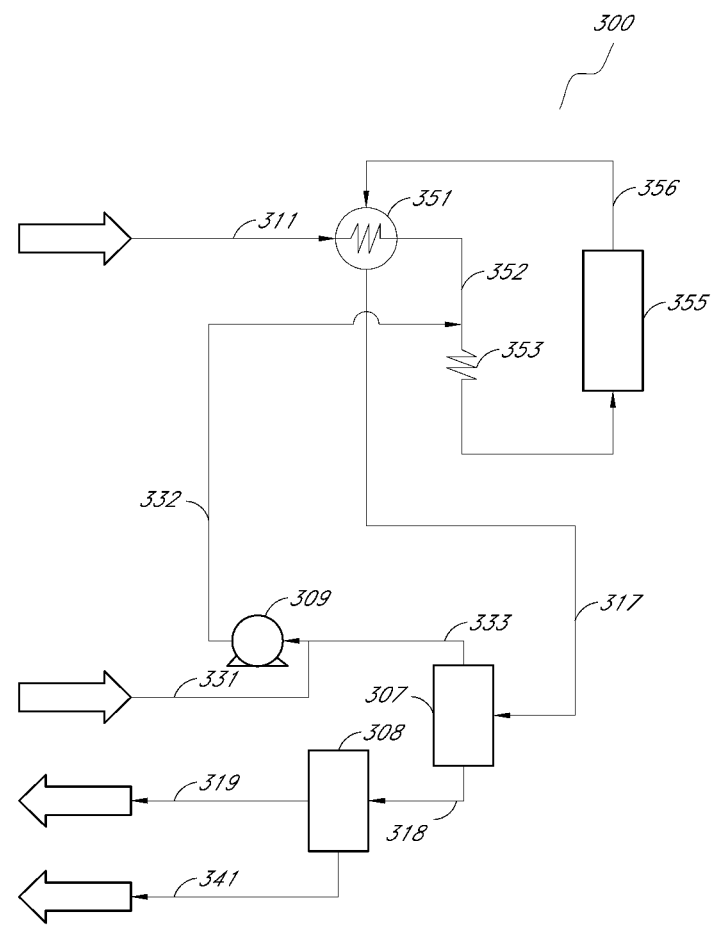
FIG. 2a is a schematic diagram of a process of FIG. 2 showing some optional heat exchangers and blower.

In other embodiments, various heat exchangers, vaporizers, coolers, condensers, blowers, and pumps can be used in the process. FIG. 2a shows schematically one such embodiment with recuperative heat exchanger 351, heater 353, and blower 309. In different configurations, variations can be used, such as where recuperative heat exchanger 351 and/or heater 353 can be incorporated into reactor 355. Similarly, coolers and/or condensers can be integrated into condensing separator 307, or be made separate.

Water Gas Shift Hydrogen Supplementation

The water-gas shift reaction represents an equilibrium between carbon monoxide and water on one side of the equation, and carbon dioxide hydrogen on the other:

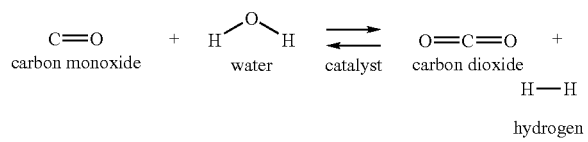

The catalyst is preferably selected so as to reduce the operating temperature for this reaction. The reaction itself is well known, having been studied for many years. Suitable catalysts include those based on Fe/Cr, Cu/ZnO, Pt/Ce, and sulfides of Co/Mo. Different catalysts result in different temperature requirements for the reaction. For example, typical operating temperatures when Fe/Cr catalyst is employed are in excess of about 350° C., while those for Cu/ZnO are typically from about 200° C. to about 300° C., and those for Pt/Ce are typically from about 200° C. to about 500° C. Some of the catalysts require the presence of additional chemicals or agents to maintain activity. For example, sulfides of Co/Mo require the presence of sulfur in the reaction stream to maintain activity. In certain embodiments, these agents can be added to the reaction mixture, they can be carried over from an earlier processing step with one of the reagents, such as for example, sulfates or sulfuric acid being present in a glycerol feedstream after acid catalyzed transesterification with sulfuric acid, or the agent can be left out, and provision made for periodic regeneration of the catalyst. The agent can be removed in a downstream process step, or left in the product stream. In some embodiments, the agent is preferably recycled. As the catalysts are identified, their temperature requirements can be readily ascertained, and employed within the process for producing alcohol.

The water gas shift reaction can be operated over a broad range of pressures. Typically, it is run at a pressure of from about 1 bar to about 20 bar. While the equilibrium is not strongly affected by the pressure, the reaction rate increases as the pressure increases due to increased collisions between molecules. Operation outside of this range is also possible, and the actual operating pressure can be selected based on other parameters such as, for example, the pressure requirements for processing steps upstream or downstream of the shift reactor.

Figure 3:
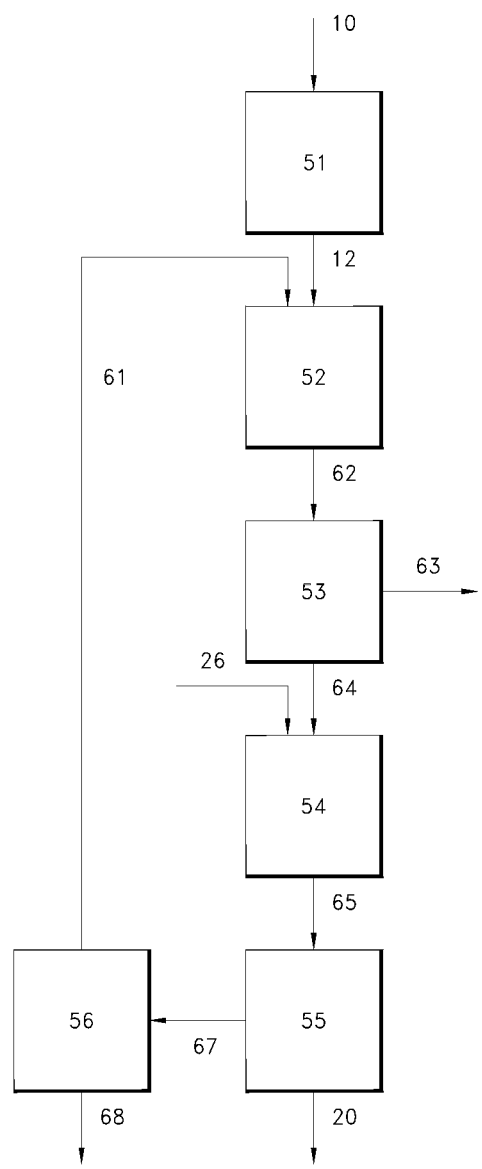
FIG. 3 is a schematic diagram of a process for converting glycerol to monohydric alcohols which incorporates a water-gas shift reaction into the process.

As shown in FIG. 3, a water-gas shift reaction can be employed to provide hydrogen for the process. In the dehydration and hydrogenation reactors, side reactions can occur under various conditions which resulted in the formation of carbon monoxide which when present can be recovered and recycled with residual hydrogen. In one embodiment, the side product carbon monoxide with residual hydrogen 61 is recycled to the process downstream of the first reaction step 51. While FIG. 3 depicts a water-gas shift reactor 52 employed in a system with a combined bed reactor and a hydrogenation reactor, it can be employed in any of the processes disclosed herein which utilize hydrogenation and have, or can be made to have, carbon monoxide (CO) present. As such, it can optionally be employed to provide or supplement the hydrogen for the process downstream of a dehydration reaction step, or a combined reaction step, or downstream of an oxidative cleavage step. If one of these reaction steps is present, the water-gas shift reaction system can be fitted to a recycle stream where CO and water is present. In certain embodiments, the process conditions can be adjusted to ensure sufficient carbon monoxide is present for the amount of hydrogen to be made with the water-gas shift reaction. In various embodiments, the process conditions can be adjusted to ensure most of the carbon monoxide present undergoes the water-gas shift reaction to produce hydrogen for the process.

In the water-gas shift reaction integrated into the process shown in FIG. 3, carbon monoxide combines with water in a reactor 52 over a catalyst to produce hydrogen gas, carbon dioxide and water 62. The hydrogen rich stream 62 is then separated 53 to remove water 63. The water depleted stream 64 is fed to the second reactor 54 for hydrogenation, in some embodiments with additional hydrogen 26 from the water-gas shift system or from elsewhere. The hydrogenated mixture 65 is separated to remove the alcohols and the gas stream 67, primarily composed of hydrogen, carbon monoxide and carbon dioxide, is separated 56 by pressure swing adsorption to remove carbon dioxide 68, with the hydrogen and carbon monoxide recycled as stream 61.

The pressure swing adsorption unit 56 includes a zeolite-based adsorbent material which adsorbs $CO_2$ at high-pressure and desorbs it when the pressure is reduced. The $CO_2$ depleted stream can be recycled as a source of hydrogen and CO within the process. The purged $CO_2$ stream can be vented to the atmosphere, or collected if desired. The high-pressure conditions are preferably from about 3 bar (absolute) to about 11 bar (absolute). Preferably, the low-pressure condition is at or near atmospheric pressure. However, pressures higher or lower can be employed as long as the pressure is less than the high-pressure condition. If sub-atmospheric pressure is employed, blowers and/or compressors may be required to handle the low-pressure gas stream.

Other operating steps in this embodiment, such as for the first reactor 51, the separation steps 53, 55 and the hydrogenation reactor 54 are largely similar to that described in other embodiments. In some circumstances, somewhat different stream compositions can be employed. For example, the recycle of carbon monoxide and subsequent conversion of carbon monoxide to carbon dioxide in the water-gas shift reaction can increase the amount of these compounds in the system.

FIG. 1, as described above, also illustrates as a block diagram one embodiment of a process for converting polyhydric alcohols including glycerol and glycols to monohydric alcohols. A feed material 10 which includes glycerol and water is reacted in a first reaction step 1 to at least partially dehydrate glycerol in the feedstream. The feed material is either in gaseous form or it is vaporized inside the reactor or prior to entering the reactor. Vaporization can be accomplished by increasing the temperature or reducing the pressure of the stream, or by a combination of raising the temperature and lowering the pressure. Suitable temperatures are from about 200° C. to about 400° C. and suitable pressures are from about 1 bar to about 7 bar (absolute). Preferred conditions for production of a 1-propanol rich product include temperatures of about 265° C. to about 305° C. and pressures of about 4 to about 7 bar (absolute). Preferred conditions for production of a mixed alcohol stream, such as one including methanol, ethanol and 1-propanol include temperatures of from about 250° C. to about 305° C. and pressures of about 1 bar (absolute).

The dehydration product stream 12 exits the reaction step and enters a first separation step 2. The dehydration product stream 12 is at least partially condensed to produce a liquid stream 13 which contains at least a portion of the water present in the reacted stream 12. Liquid stream 13 can also contain at least some of the impurities present that are present in the feedstream 10 or generated in the reaction step 1. Condensation in separation step 2 can be accomplished by reducing the temperature or raising the pressure, such as by compressing the gas, or by a combination of cooling and increasing the pressure. Such cooling and/or pressure increase can be accomplished within the separation step 2 or prior to the reacted stream 12 entering the separation step 2. Hydrogen 25 can also be added to the separation step. Hydrogen 25 added at this point can participate in the separation that takes place, for example, by sweeping gas headspace present in the separation device or by reducing the partial pressure of other components in the separation step 2.

The gaseous stream 14 leaves the separation step 2 and enters the second reaction step 3. In the second reaction step 3, the gaseous stream 14, which can include aldehydes and alcohols, acetones and acrolein, reacts with hydrogen over a hydrogenation catalyst as previously described in an exothermic reaction. The hydrogen can be introduced in the first separation step 2, or at the second reaction step 26, or at both. The hydrogen can also be added in portions, as with a multistage reaction step where a portion of the hydrogen is added and allowed to react, then an additional portion of hydrogen is added and allowed to react. The sequence of adding hydrogen and reacting can be repeated for additional stages of reaction. Optionally, the temperature of the reaction mixture can be limited, reduced, or controlled by any suitable method and/or apparatus, such as by cooling the gaseous feed 14, cooling the equipment such as with cooling jackets or coils, or adding cooling equipment between the stages of the reaction step.

The reacted material stream 16 exits the second reaction step 3 and enters the second separation step 4. The reacted material stream 16 is at least partially condensed to produce a product stream 20 which contains at least one monohydric alcohol. The noncondensed material 27 can contain nonreacted glycerol, incompletely reacted intermediates, such as aldehydes, acrolein, hydroxy acetone, and other compounds. Condensation in the second separation step 4 can be accomplished by reducing the temperature or raising the pressure, such as by compressing the gas, or by a combination of cooling and increasing the pressure. Such cooling and/or pressure increase can be accomplished within the separation step 4 or prior to the reacted material stream entering the second separation step 4.

The nature of the separation that occurs in the second separation step 4 can be adjusted depending upon the operating temperature and pressure. For example, as the temperature is decreased, the pressure increased, or both, more materials are condensed and the composition of the product stream 20 and the noncondensed 27 stream change.

Figure 4:
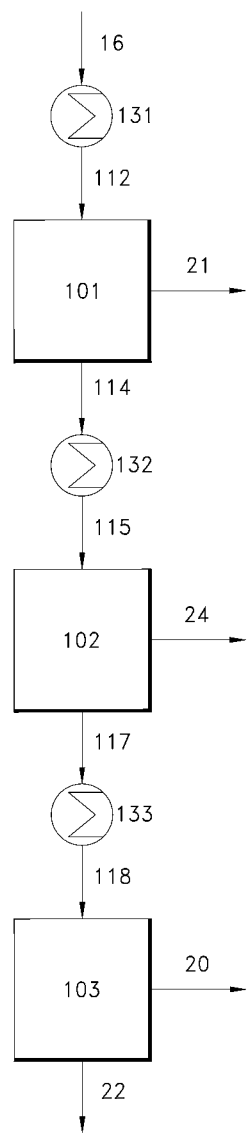
FIG. 4 is a block diagram of an embodiment of the second separation step of FIG. 1 which depicts a three-step separation process.

In certain embodiments, the second separation step 4 can be operated as a multistage condensation with different liquid materials removed under different condensation conditions to accommodate, for example, different products, to provide better selectivity or better purity of a particular stream, or to better facilitate recycle of streams. Two, three, or more stages can be employed. In certain embodiments, more than one stage can use the same conditions. FIG. 4 illustrates an embodiment of a multistage second separation step that includes three condensation steps. The reacted material stream 16 is cooled with cooling step 131, and enters the first stage separation step 101. Liquid stream 21, which includes glycols, is removed from the gaseous stream 114. The operating conditions of first stage separation step 101 are, for operation at 1 atmosphere, a temperature of preferably from about 150° C. to about 185° C. based on the boiling points of glycerol, propylene glycol, ethylene glycol and hydroxyacetone. For operation at other pressures, the temperature can be adjusted based on the change in boiling point of the materials being separated.

Gaseous stream 114 is further cooled in cooling step 132 and enters the second stage separation step 102. Liquid stream 24, which includes hydroxyacetone, is removed from the gaseous stream 117. The operating conditions of second stage separation step 102 are, for operation at 1 atmosphere, preferably about 100° C. to about 143° C. based on the boiling points of hydroxyacetone and the monohydric alcohols present. If little or no 1-propanol is present, a temperature of from about 80° C. to about 143° C. is employed. For operation at other pressures, these temperatures can be adjusted based on the difference in boiling point of the materials being separated.

Gaseous stream 117 is further cooled in cooling step 133 and enters third stage separation step 103. Liquid stream 20 which includes one or more monohydric alcohols is removed from the gaseous stream 22 which includes hydrogen gas. The operating conditions of third stage separation step 103 are, for operation at 1 atmosphere, a temperature of preferably from about 58° C. to about 62° C., depending upon the boiling points of the monohydric alcohols present and the aldehydes and ketones present. In certain embodiments, the presence or absence of particular compounds enables operation at somewhat different temperatures. For example, if there is little or no acetone present, but acrolein is present, the low end of the temperature range can be as low as about 55° C. Similarly, if little or no acetone or acrolein is present, the low end of the temperature range can be as low as about 52° C. For operation at other pressures, these temperatures can be adjusted based on the difference in boiling point of the materials being separated.

Figure 5:
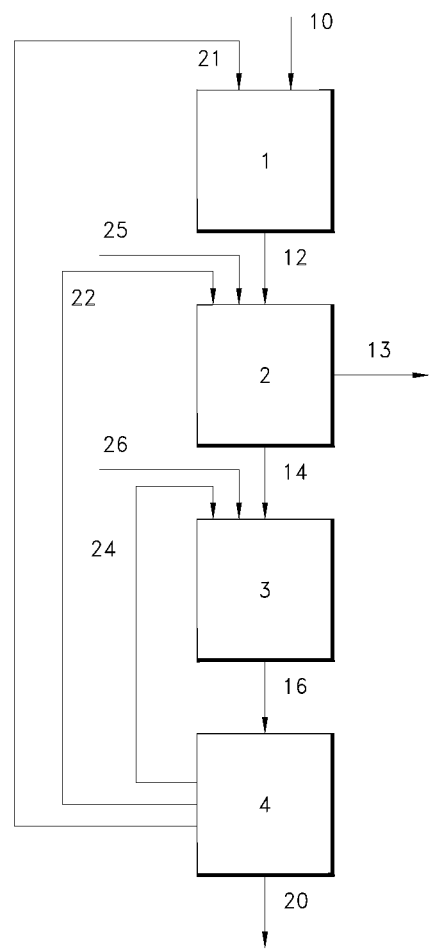
FIG. 5 is a block diagram of a process for converting glycerol to monohydric alcohols where the process includes recycling of unreacted/partially reacted species.
Figure 6:
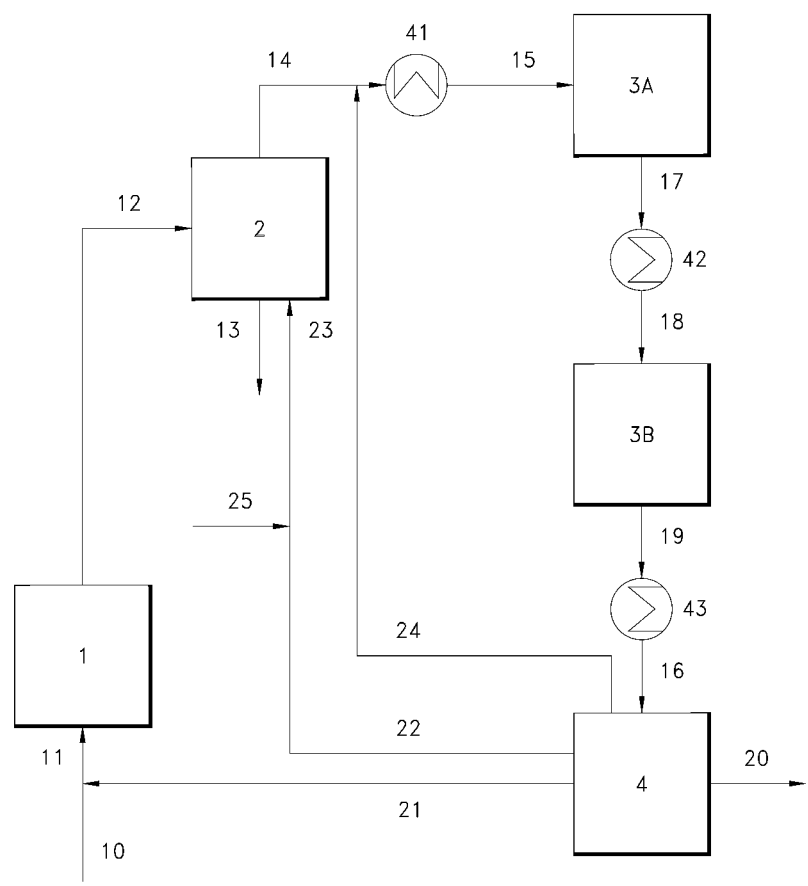
FIG. 6 is a block diagram of the process for converting glycerol to monohydric alcohols where the hydrogenation reaction step takes place in two steps.

In further embodiments, materials separated from the process can be recycled back into the process. FIG. 5 shows one embodiment wherein the streams from a three stage second separation step 4, such as is shown in FIG. 3, are recycled into the process. Liquid stream 21 is recycled to the first reaction step 1. Gaseous stream 22 is recycled to the first separation step 2. Liquid stream 24 is recycled to the second reaction step 3. FIG. 6 shows another embodiment where the second reaction step takes place in two-steps 3A and 3B. In addition, optional heat exchange devices 41, 42, and 43 are used to adjust the temperature of the feed 15 to the reactor 3A, and intermediate stream between reactor stages 17 and the final reacted stream 16 from the second reaction step. Optional heat exchange devices 41, 42, and 43 can be used, for example, as inter-coolers between stages within reactor 3, or as heaters if desired. Such heat exchange devices, when used, can be present between some reactor stages and absent between others or they can be present between all reactor stages.

Alternative embodiments can optionally include steps such as routing the gaseous stream 22 to the first reaction step 1, and routing the gaseous stream 22 to the second reactor step 3. When gaseous stream 22 is recycled within the process, it may permit a reduction in the amount of hydrogen added at 25 or 26, in that the product is already at least partially hydrogenated. Other streams can be directed to other locations as well. For example, liquid stream 24 can be recycled to the first reaction step 1.

Recycle of process streams and fractions thereof can also be employed elsewhere in the process. For example, with a single stage second separation step, gaseous stream 22 can be recycled as described above.

Additional embodiments include storage of the liquid streams removed from the second separation step 4 and processing of the stream at a different time or location. The material separated can be recycled into the process at a later time or run in the process separately from fresh glycerol feed material.

In other embodiments, hydrogen can be generated on-site for use in the process. The hydrogen can be generated, for example, internally within the combined reactor bed 1 by integrating a small amount of reforming catalyst, such as are known to those having skill in the art, into the mixed catalyst bed, or at the start of the mixed catalyst bed. This approach could provide a small amount of hydrogen, such as is needed to convert the acrolein into propionaldehyde but insufficient amounts to promote the production of monohydric alcohols.

Figure 7:
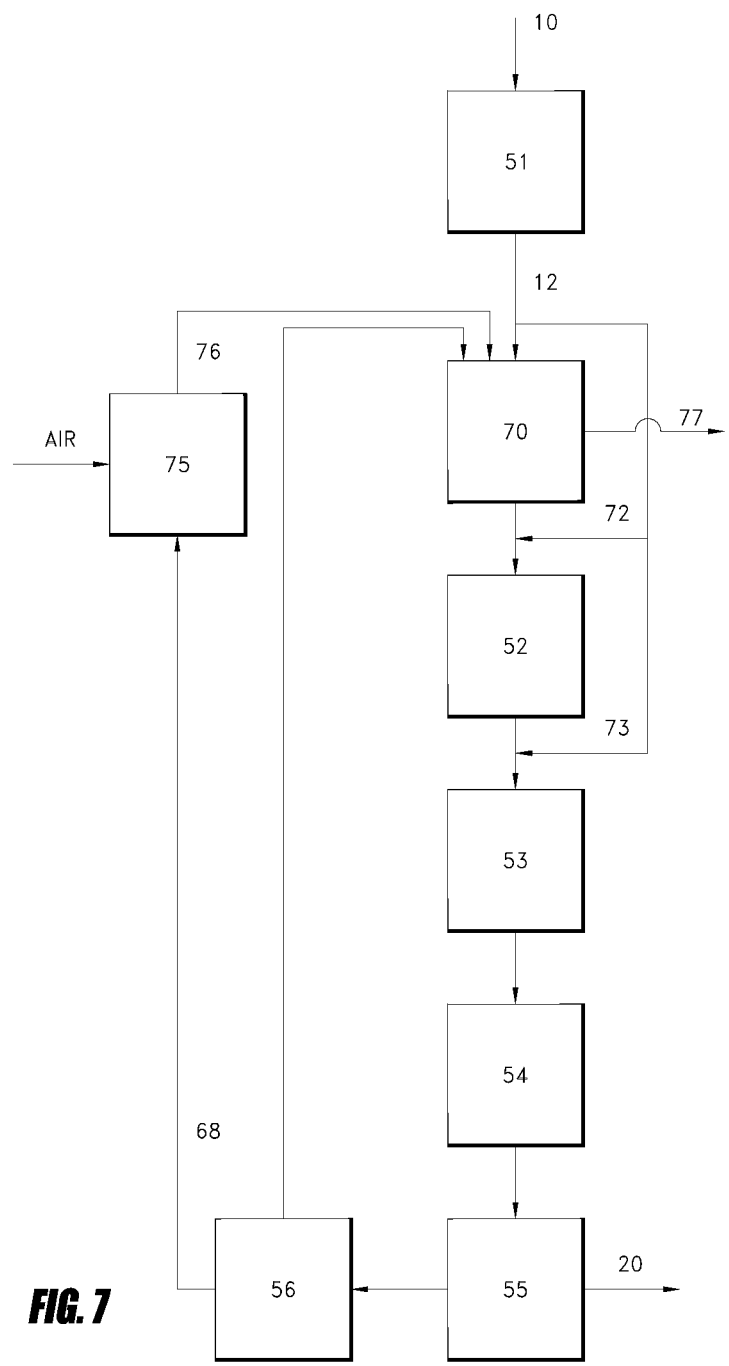
FIG. 7 is a block diagram of a process for converting glycerol to monohydric alcohols which utilizes steam reforming of at least a portion of an intermediate process stream to generate at least a portion of the hydrogen used in the process.

In other embodiments, larger amounts of hydrogen can be generated on-site in other configurations as illustrated in FIG. 7. In FIG. 7 hydrogen is formed by steam reforming a portion of the intermediate stream after the first reactor 51 to hydrogen and carbon monoxide but prior to the first separation step. This hydrogen is then available to hydrogenate other compounds within a later hydrogenation step. The presence of aldehydes and acroleins after the first reactor makes this stream well-suited for steam reforming, especially when water vapor is present as well. To control the amount of hydrogen generated and the amount of intermediate products consumed, in one embodiment, a portion of the first reactor 51 outlet stream 12 is diverted as stream 71. This diverted stream can be reintroduced prior to the water gas shift reactor 52 as stream 72 or after the water gas shift reactor as stream 73, depending on the amount of carbon monoxide byproduct generated in the first reactor 51. Another advantage of this configuration is its integration with the gas phase separation 56 which can be, for example, a pressure swing adsorption unit. After the second separation step 55 in which the product liquids 20 are isolated from the gaseous compounds, the gaseous stream 56 is passed to a gas phase separation to remove carbon dioxide from hydrogen and carbon monoxide. To achieve removal of the majority of the carbon dioxide, some hydrogen and carbon monoxide can exit with the exhaust stream 68. These gases can combusted in reactor 75 to generate heat which is needed for the endothermic steam reforming step in reactor 70. With this configuration, an overall increase process efficiency can be achieved and hydrogen can be eliminated or reduced as a feedstock from the process.

In certain embodiments, the process is tailored to employ a dilute glycerol solution. For example, a 20 wt. % glycerol solution is fed to a first combined dehydration and hydrogenation reactor, at a pressure of from about 5 bar (absolute) to about 7 bar (absolute). The inlet temperature of the combined reactor is from about 280° C. to about 300° C. and the glycerol/water mixture is co-fed with hydrogen. The introduction of hydrogen into the reactor enables a lower inlet temperature to be employed than if acrolein was to be produced. Balancing the endothermic dehydration of glycerol to acrolein with the hydrogenation of acrolein to propionaldehyde yields a more even temperature gradient over the dehydration section of the mixed bed reactor. The far end of the combined reactor can be configured for a final hydrogenation wherein the temperature is increased to from about 350° C. to about 400° C. This elevated temperature provides benefits such as better heat exchange of the outlet with the inlet streams, and suppression of the formation of 1-propanol in the reactor due to the equilibrium that is maintained.

After leaving the combined reactor, the gaseous reaction mixture consisting of water, propionaldehyde, acrolein and traces of other byproducts such as propionic acid and hydroxyacetone is cooled. After cooling, the gas is mixed with a surplus of hydrogen and carbon monoxide and is passed through a water-gas shift reactor where the carbon monoxide is reacted with water to form carbon dioxide and hydrogen.

Figure 8:
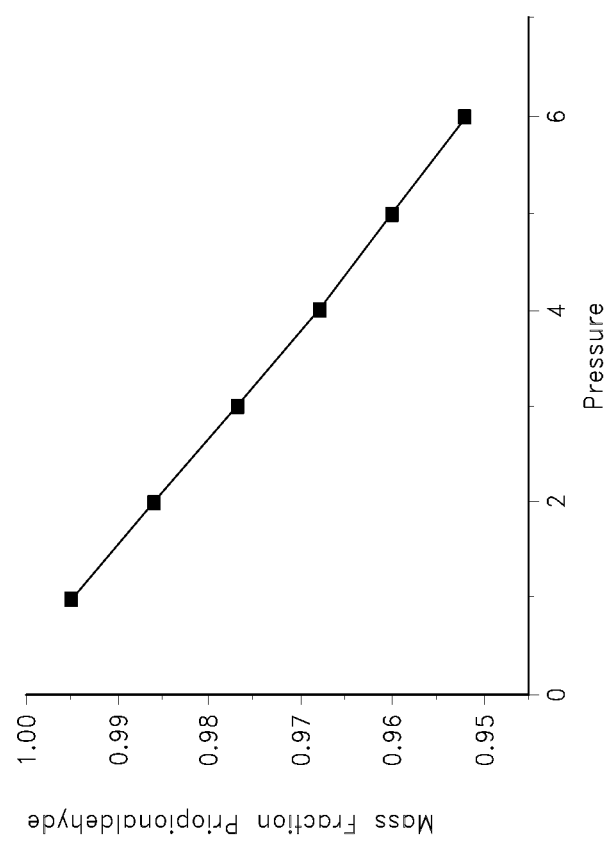
FIG. 8 is a graph showing the azeotropic composition of water-propionaldehyde at different pressures.

The reaction mixture is then cooled further and introduced into a distillation column. The distillation of the mixture can be conducted in a regular distillation column, where it is distilled at about the system operating pressure. This yields a top volatile fraction rich in propionaldehyde. Purity of the propionaldehyde (also known as propanal) stream may be limited by a propionaldehyde-water azeotrope, as shown in FIG. 8.

The separation can be further improved by the use of hydrogen as a sweep gas. Many high boiling compounds, such as propionic acid and the like, can be removed in the still bottoms along with water. Carry-over of intermediate boiling components is more dependent upon the column design and operation.

The volatile stream from the distillation typically contains mainly propionaldehyde and a small amount of water. This stream can be reheated using heat within the process or from an external source, and introduced into a hydrogenation reactor. In the hydrogenation reactor, propionaldehyde and acrolein are reacted to form 1-propanol. Other shorter chain aldehydes are also reacted to form ethanol and methanol. The reaction is exothermic by nature and the reaction products are cooled, for example, in a constantly cooled tube reactor or several reactors with inter-cooling, using the inlet glycerol/water mixture. In the hydrogenation reactor there is some formation of byproducts such as propionic acid, dipropylether, and carbon monoxide. The residence time, catalyst and temperature in this reactor, as well as the chemical species present, determines the amount of carbon monoxide and other compounds formed. The resulting stream contains 1-propanol, ethanol, methanol, water, surplus hydrogen, carbon monoxide, carbon dioxide, and traces of byproducts such as propionic acid. The resulting mixture is passed through a condenser where 1-propanol, other short chain alcohols, water, and byproducts are separated out and the resulting solution has 1-propanol content above 90% by weight.

The non-condensing gases are led to a pressure swing adsorber (PSA) where the carbon dioxide is separated together with a small part of the carbon monoxide and hydrogen, while the rest of the hydrogen and carbon monoxide is recirculated to the process.

Integration of the Water-Gas Shift Reaction into Production of Monohydric Alcohol from Glycerol The water-gas shift reaction enables hydrogen gas to be generated from carbon monoxide and water. Conversion of glycerol to monohydric alcohols requires hydrogen. FIGS. 3 and 7 illustrate a process for converting glycerol to monohydric alcohol which utilizes the water-gas shift reaction to supply at least a part of the necessary hydrogen. In certain embodiments, this conversion can take place by converting glycerol to acrolein, and then acrolein to propionaldehyde prior to the final conversion to 1-propanol. These first two-steps are shown below:

$$C_3H_8O_3 \rightarrow C_3H_4O + 2H_2O$$

(Dehydration of Glycerol to Acrolein—Endothermic)

$$C_3H_4O + H_2 \rightarrow C_2H_6O$$

(Hydrogenation of acrolein to propionaldehyde—exothermic)

These two reactions can take place in the combined reactor with a combined dehydration and hydrogenation catalyst supplied with hydrogen. If about 60% to about 80% of the acrolein is converted to propionaldehyde, the reaction is autothermal (the endothermic reaction heat requirements are fulfilled by the exothermic reaction).

The efficiency of the conversion of glycerol to monohydric alcohols, such as 1-propanol, with the hydrogen provided by the water-gas shift reaction can be evaluated as described below. Analysis of other species is analogous, with a similar overall efficiency.

In the first step, glycerol is converted to carbon monoxide and hydrogen:

$$C_3H_8O_3 \rightarrow 3CO + 4H_2$$

(Reforming of Glycerol)

This reaction is subsequently followed by the water-gas shift reaction:

$$3CO + 3H_2O \rightarrow 3CO_2 + 3H_2$$

(Water-Gas Shift Reaction)

A total of 7 $H_2$ molecules are formed for each glycerol molecule converted. This hydrogen is then available in the reaction of glycerol to propionaldehyde (equations shown above) and for the hydrogenation of the propionaldehyde to 1-propanol:

$$C_3H_6O + H_2 \rightarrow C_3H_7OH$$

(Formation of 1-Propanol)

The net equation for conversion of glycerol to 1-propanol with production of hydrogen by glycerol is:

$$9C_3H_8O_3 \rightarrow 7C_3H_7OH + 8H_2O + 6CO_2$$

(glycerol to propanol with internal hydrogen generation)

The net equation shows the theoretical value for conversion efficiency of glycerol to 1-propanol to be seven-ninths, or about 80%. Actual efficiency is likely lower (e.g., about 60% or less). Conversion efficiencies of glycerol to other monohydric alcohols can be determined in a similar fashion, and similar efficiencies are expected.

Gas Phase Oxidative Production of Methanol and Ethanol

Figure 9:
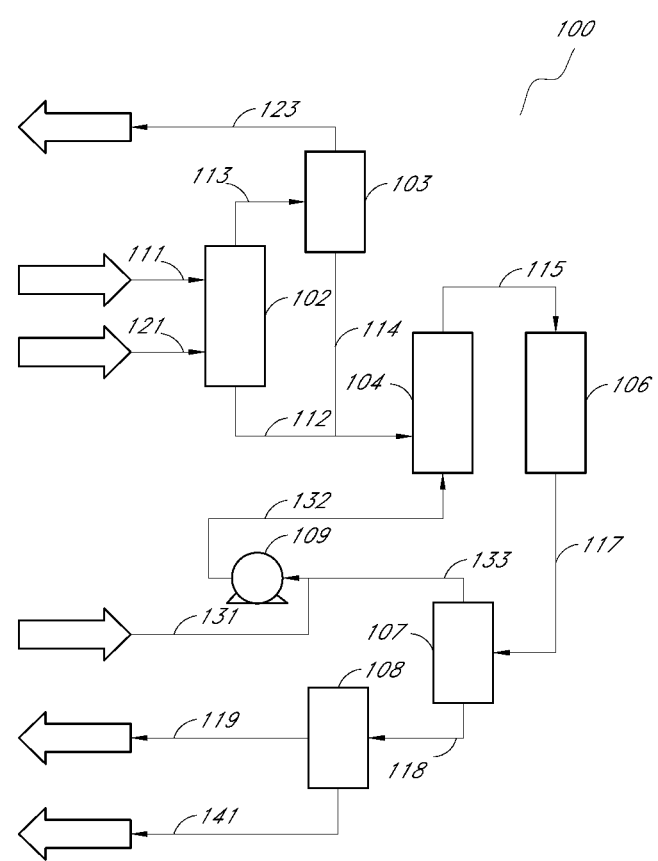
FIG. 9 is a block diagram of a process for converting glycerol to monohydric alcohols utilizing an oxidative cleavage step followed by hydrogenation and dehydration reactions.

FIG. 9 schematically illustrates a gas phase glycerol conversion process of a preferred embodiment wherein glycerol is converted into a methanol-ethanol mixture of alcohols by a gas-liquid phase process 100 employing intermediate aldehyde compounds and relatively low temperatures, e.g., under 400° C. In this embodiment, the glycerol 111 is fed to an oxidative cleavage reactor 102 along with a source of oxygen, such as air 121. Suitable catalysts (e.g., rhodium or chromium) support the oxidative cleavage of the carbon-carbon bond in vicinal diols, producing smaller aldehydes:

$$R_1(CHOH)(CHOH)R_2 + \tfrac{1}{2}O_2 \rightarrow R_1CHO + R_2CHO + H_2O$$

Wherein $R_1$ and $R_2$ are independently selected from the group consisting of hydrogen, $C_{1-4}$ alkyl, $C_{1-4}$ alkene, $C_{1-4}$ alkyne, $C_{1-4}$ hydroxyalkyl, $C_{1-4}$ hydroxyalkene, $C_{1-4}$ hydroxy-alkyne, benzyl, phenyl, substituted benzyl, and substituted phenyl groups.

To produce alcohols, the aldehydes can be reduced with hydrogen gas over a suitable catalyst. Catalysts for hydrogenation are the same as discussed previously. The hydrogenation reaction is represented by the following reaction scheme.

$$R-CHO + H_2 \rightarrow R-CH_2OH$$

When the starting material is glycerol, the first reaction step involves formation of formaldehyde ($CH_2O$) and glycolaldehyde (2-hydroxyethanal, $CHOCH_2OH$), such as through a partial oxidation reaction with oxygen in a gas-liquid phase relatively low temperature, low pressure catalytic reactor. Typically the oxygen can be obtained from air, purified air, pure oxygen, or a combination thereof. If air or oxygen-depleted air is used, nitrogen will flow through the process as a dilution gas. If pure oxygen is desired the oxygen can be removed from air with a variety of known methods including pressure swing adsorption, membrane techniques, electrochemical techniques, and others. Electrochemical techniques can provide an active catalyst surface with the ability to precisely regulate the quantity of oxygen present at the catalyst surfaces. The oxygen cleavage reaction is the following:

$$C_3H_5(OH)_3 + \tfrac{1}{2}O_2 \rightarrow CH_2O + CHOCH_2OH + H_2O$$

As shown in FIG. 9, glycerol 111 and oxygen source (for example, air) 121 are fed to the oxidative cleavage reactor 102 where the triol is converted to formaldehyde and glycolaldehyde. The reaction is exothermic and the catalyst reactor is managed at temperatures of from about 100° C. to about 400° C. Suitable catalysts include various rhodium, chromium or other salts in homogenous phase, in solid form, or supported on solid material such as alumina, silica, carbon, and the like. Since the formaldehyde and water have low boiling points, the formaldehyde and water are vaporized with heat from the reaction and purged from the reactor with depleted air to condenser-separator 103, in which the vaporized aldehyde and water are condensed and removed through connection 114 and the depleted air is passed out of the process in stream 123. Alternatively, if all the oxygen is reacted, the nitrogen from the depleted air can also flow through stream 114 and function as dilution gas. Since the glycolaldehyde has a much higher boiling point, it remains in the liquid phase along with non-reacted glycerol. When the liquid phase has undergone sufficient conversion (sufficient resident time in a tank or reaction time in a batch reactor) to convert most if not all of the glycerol, the glycolaldehyde remains as a liquid and exits the reactor 102 through connection 112, is mixed with the condensed formaldehyde-water stream 114 and is fed to the reduction-hydrogenation reactor 104. In one embodiment, a reactive distillation column can be used for the oxidative cleavage step 102.

The second step is a combined hydrogenation/dehydration step in the reactor 104, wherein the aldehydes are reduced to alcohols. The formaldehyde reacts with hydrogen to form methanol according to the following reaction.

$$CH_2O + H_2 \rightarrow CH_3OH$$

The glycolaldehyde also reacts with hydrogen to form the intermediate ethanediol (ethylene glycol, $HOCH_2-$ CH$_2$OH), which can be further dehydrated and hydrogenated to produce ethanol. The dehydration step results in the formation of vinyl alcohol (CH$_2$=CHOH) and water, which further reacts with hydrogen to form ethanol. The resulting stream of methanol, ethanol, and water is removed from the process. The reaction steps are as follows.

CHO—CH$_2$OH+H$_2$→HOCH$_2$—CH$_2$OH

HOCH$_2$—CH$_2$OH→CH$_2$=CHOH+H$_2$O

CH$_2$=CHOH+H$_2$→CH$_3$CH$_2$OH

As shown in FIG. 9, the mixed aldehyde solution enters the reduction-hydrogenation reactor 104 in which the formaldehyde reacts to form methanol and the glycolaldehyde reacts to form ethanediol. This gas-liquid stream is passed to the hydrogenation-dehydration reactor 106 in which the water is chemically removed from the diol followed by the hydrogenation to form ethanol. The mixed stream 117 consisting of methanol, ethanol, water, trace non-reacted compounds, and hydrogen, flows to the condenser-separator 107. The hydrogen gas 133 is separated from the liquids, mixed with feed hydrogen 131 and is passed to pump 109, in which pressure is increased and the feed hydrogen is passed to reactor 104. The liquids are passed to water separator 108 in which water is isolated from the mixed alcohol stream and removed. The water separation can be a distillation and/or a desiccation process. The product alcohol stream 119, which is primarily ethanol and methanol, can be fed to a biodiesel reactor 2 to supplement or replace a fresh alcohol feedstream.

Periodate Route for Production of Alcohols (Methanol)

A liquid phase oxidation scheme using periodate ion can also be used to oxidatively cleave the polyhydric alcohol to carbonyl-containing compounds in a reaction analogous to the oxidation described above.

R$_1$—CHOH—CHOH—R$_2$+IO$_4^-$→R$_1$—CHO+R$_2$—CHO+IO$_3^-$+H$_2$O

However, regeneration of the periodate ion does not readily occur by oxidation with air or oxygen, but can be achieved through an electrochemical mechanism.

It has now been found that a continuous process for oxidative cleavage of polyols using periodate ion can advantageously be employed when an external electric source for regeneration as an electrolytic cell is provided. The half reactions are as shown below.

Anode:IO$_3^-$+H$_2$O→IO$_4^-$+2H$_2^+$+2e$^-$

Cathode:2H$^+$2e$^-$→H$_2$(g)

Operation of the cleavage reaction in an electrolytic cell permits simultaneous oxidative cleavage of a polyhydric alcohol, such as glycerol, and regeneration of the periodate ion. Subsequent hydrogenation of the carbonyl containing compounds, such as formaldehyde, can be carried out as described elsewhere to produce monohydric alcohols.

The net reaction is:

R$_1$—CHOH—CHOH—R$_2$→R$_1$CHO+R$_2$—CHO+H$_2$ wherein R$_1$ and R$_2$ are as defined above. The hydrogen generated during the cleavage can be used to convert the carbonyls to alcohols, such as by methods described herein. Alternatively, the hydrogen can be used for other purposes including as a fuel and as a reagent in other reactions.

Gas Phase Production of Methanol by Oxidative Cleavage

If the second reaction step of the gas phase oxidative production of methanol and ethanol, described herein, is changed from a hydrogenation/dehydration step to a hydrogenation step solely, after one pass through the two reactors, glycerol is converted primarily to ethanediol and methanol. These compounds are readily separated by various means including, for example, distillation due to the difference in their boiling points. The diol can then be returned to the oxidative cleavage step and split into formaldehyde.

HOCH$_2$—CH$_2$OH+½O$_2$→2CH$_2$O+H$_2$O

Figure 10:
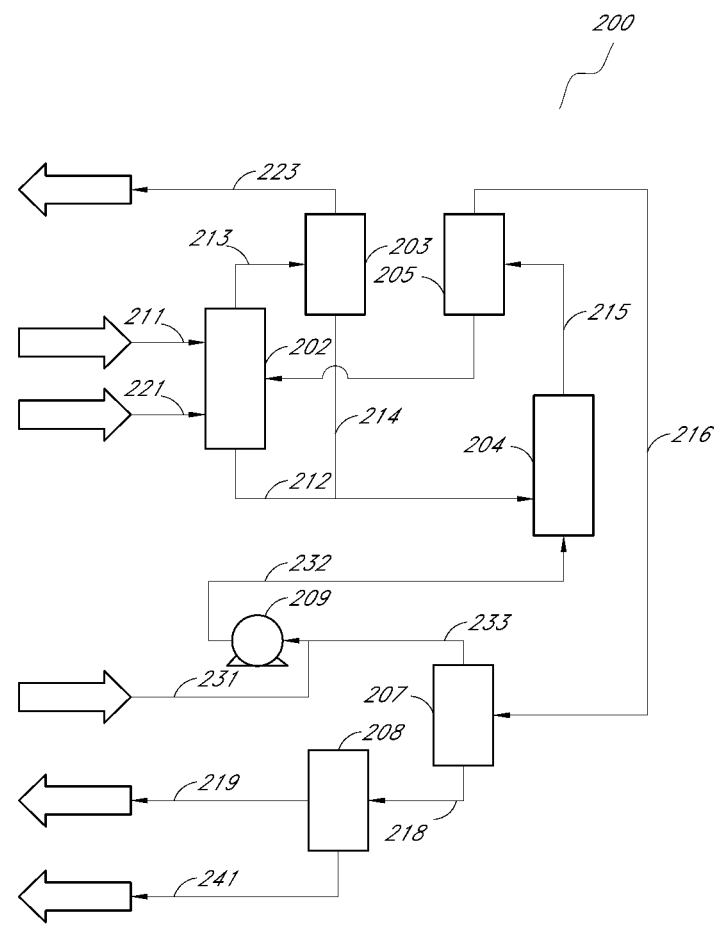
FIG. 10 is a block diagram of a process for converting glycerol to methanol utilizing oxidative cleavage followed by a hydrogenation reaction without a dehydration reaction.

FIG. 10 is block diagram depicting such a process schematically. Glycerol 211 and air 221 are reacted in an oxidative reactor 202. The depleted air with some volatile species 213 is condensed 203 to recover reacted intermediates 214. The depleted air 223 is removed or can pass through the process as a dilution gas. The reaction mixture 212 from the oxidative reactor 202 is combined with stream 214 and fed to hydrogenation reactor 204 with hydrogen stream 232. The gaseous reaction products and unreacted hydrogen 215 are separated in condenser 205. The liquid phase containing ethanediol is returned to the oxidative reactor 202. The gas phase 216 containing methanol, hydrogen, and other gases are separated in condenser 207. The hydrogen-rich gas phase 233 is mixed with additional hydrogen 231 and compressed 209. The hydrogen feed 232 is sent to the hydrogenation reactor 204. The liquid phase 218 from condenser 207 is separated 208 into an alcohol-rich stream 219 and a primarily water stream 241.

Production of Hydrogen from Glycerol

Hydrogen can be generated on-site by the catalytic dehydrogenation of hydrocarbons, yielding more unsaturated hydrocarbon chains:

$$C_nH_m \rightarrow C_nH_{m-o}+\text{½}H_2 \quad (7)$$

Analogous reactions can take place with other molecules, such as alcohols, fatty acid esters, aldehydes, and ketones.

This dehydrogenation can be carried out with a nickel catalyst at low pressure and high temperature and is slightly endothermic (10 kJ/mol for C$_{12}$H$_{26}$ to C$_{12}$H$_{24}$). There are several alternative feedstocks for such a process, including glycerol and biodiesel.

In an embodiment utilizing biodiesel as the feed, a fraction of the product feed can be taken and the saturated diesel hydrocarbons can be stripped of some of their hydrogen. The size of this split-stream can be adjusted, for example, a small stream can be deeply dehydrogenated or a larger stream can be lightly dehydrogenated depending upon what product is desired. For example, if about 15% of the biodiesel product is dehydrogenated, a highly aromatic product results along with production of sufficient hydrogen to convert the glycerol to methanol for the transesterification reaction. In another embodiment, the side products from conversion of glycerol to monohydric alcohol can be employed.

In certain embodiments, the dehydrogenated hydrocarbons can be burned to supply heat for the process. Dehydrogenated compounds can also be blended into the biodiesel product, or used for other purposes as determined by their composition.

EXAMPLE 1

Combined Reactor

A liquid feed of 20% technical grade glycerol in deionized (DI) water was fed at 18 g/hr through a flowmeter to a preheater where it was vaporized and heated to approximately 290° C. The glycerol-water feed was combined with 100 ml/min (25° C., 1 atmosphere) hydrogen and fed to a reactor bed. The reacted product stream from the reactor bed was condensed and the liquid condensate analyzed. The flowrates of the condensed liquid stream and the noncondensible gases were measured. Reactor pressure was held at approximately 6 bar (absolute). The reactor bed contained two zones of catalyst. The first zone (closest to the feed inlet) contained dehydration catalyst ($WO_3/ZrO_2$, 1 mm bead). The second zone contained and equal amount of a mixture of 90% dehydration catalyst ($WO_3/ZrO_2$, 1 mm bead) and 10% hydrogenation catalyst (Topsoe, 1 mm grain).

The condensed liquid stream was analyzed by gas chromatography with a CP-3800 gas chromatograph (Varian Inc., Palo Alto, Calif.) operating with a He mobile phase. Column temperature was ramped from 80° C. to 250° C. Peaks were determined with a flame ionization detector.

The condensed liquid stream had the following composition.

| Compound | Retention time (Min.) | Quantity (Area %) |
|---|---|---|
| Acetic aldehyde | 3.24 | 11.66 |
| Propionaldehyde | 3.42 | 36.96 |
| Acetone | 3.50 | 4.96 |
| Acrolein | 3.60 | 5.08 |
| Methanol | 3.74 | 4.89 |
| Ethanol | 3.90 | 2.18 |
| Unknown | 4.17 | 1.54 |
| 1-propanol | 4.53 | 5.56 |
| 2-propanol | 5.17 | 1.72 |
| Unknown | 6.94 | 1.92 |
| Hydroxyacetone | 7.12 | 5.99 |
| Unknown | 8.13 | 1.20 |
| Propionic acid | 8.72 | 3.88 |
| Valeric acid | 9.96 | 8.57 |
| Unknown | 11.57 | 3.89 |
| Total | — | 100.00 |

EXAMPLE 2

Dehydration Reactor

The experimental set-up and operation were as described in Example 1, except that no hydrogen was added. The condensed liquid stream had the following composition and illustrates the higher production of acrolein.

| Compound | Retention time (Min.) | Quantity (Area %) |
|---|---|---|
| Acetic aldehyde | 3.23 | 2.21 |
| Propionaldehyde | 3.41 | 7.61 |
| Acrolein | 3.58 | 50.42 |
| Unknown | 4.16 | 1.33 |
| 2-pentanol | 5.16 | 4.24 |
| Hydroxyacetone | 7.11 | 23.16 |
| Valeric acid | 9.95 | 11.03 |
| Total | | 100.00 |

EXAMPLE 3

Dehydration Reactor and Hydrogenation Reactor

Figure 11:
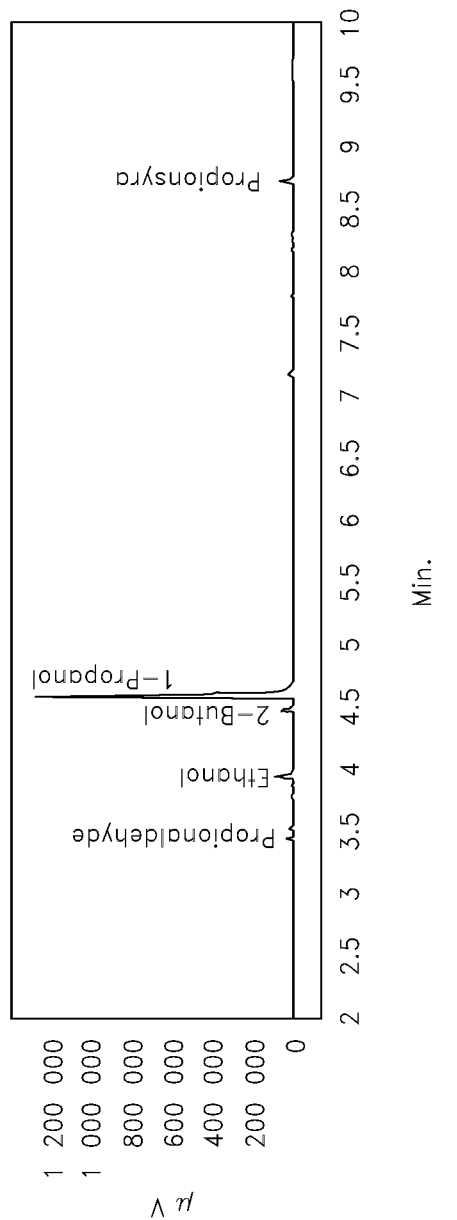
FIG. 11 is a chromatogram of the condensed product stream after performing sequential dehydration and hydrogenation on glycerol in separate reactor beds with intermediate addition of hydrogen. This figure shows the predominance of 1-propanol for reaction at 5 bar.

A solution of 20% glycerol (technical grade) in DI water at 0.3 mL/minute was heated and vaporized and fed to a first tubular reactor (25 mm diameter, 250 mm length) containing 39 mL (60 g) of 10% $WO_3/ZrO_2$ dehydration catalyst (1 mm grains), then to a second tubular reactor (12 mm diameter, 250 mm length) containing 12 mL (11 g) of Topsoe hydrogenation catalyst (1 mm grains). Between the two reactors, 400 mL/minute (1 atmosphere, 25° C.) of hydrogen was added. The first reactor inlet temperature was 307° C. and the outlet temperature was 260° C. The second reactor inlet temperature was 205° C. and the outlet temperature was 250° C. Both reactors were operated at 5 bar (absolute). After exiting the second reactor, the gas stream was condensed and the condensate analyzed by gas chromatography as in Example 1. The chromatogram is shown in FIG. 11, which indicates the high conversion to propanol.

EXAMPLE 4

Effect of Pressure

Figure 12:
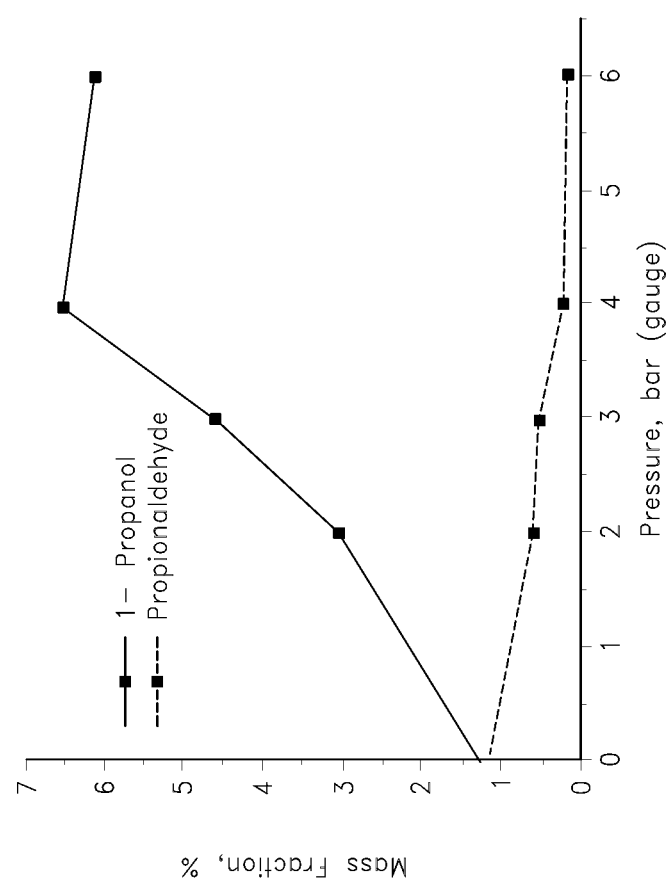
FIG. 12 is a graph of the relative concentrations of 1-propanol and propionaldehyde in the condensed product stream for conversion of glycerol to monohydric alcohols by sequential dehydration and hydrogenation with intermediate addition of hydrogen at different pressures in the reactor set-up of FIG. 1. The concentration of 1-propanol peaks, under the conditions tested, at about 4 bar (gauge).

The effect of different operating pressures on the product composition was evaluated with a reactor set up as described in Example 3. Reagents and reagents flow rates were as in Example 3. The first reactor inlet/outlet temperatures were 290° C. and 285° C., respectively. The second reactor inlet/outlet temperatures were 235° C. and 265° C., respectively. The reactor operating pressure was varied from 0-6 bar (gauge). The analytical results for 1-propanol and propionaldehyde in the product stream are shown in FIG. 12.

Figure 13:
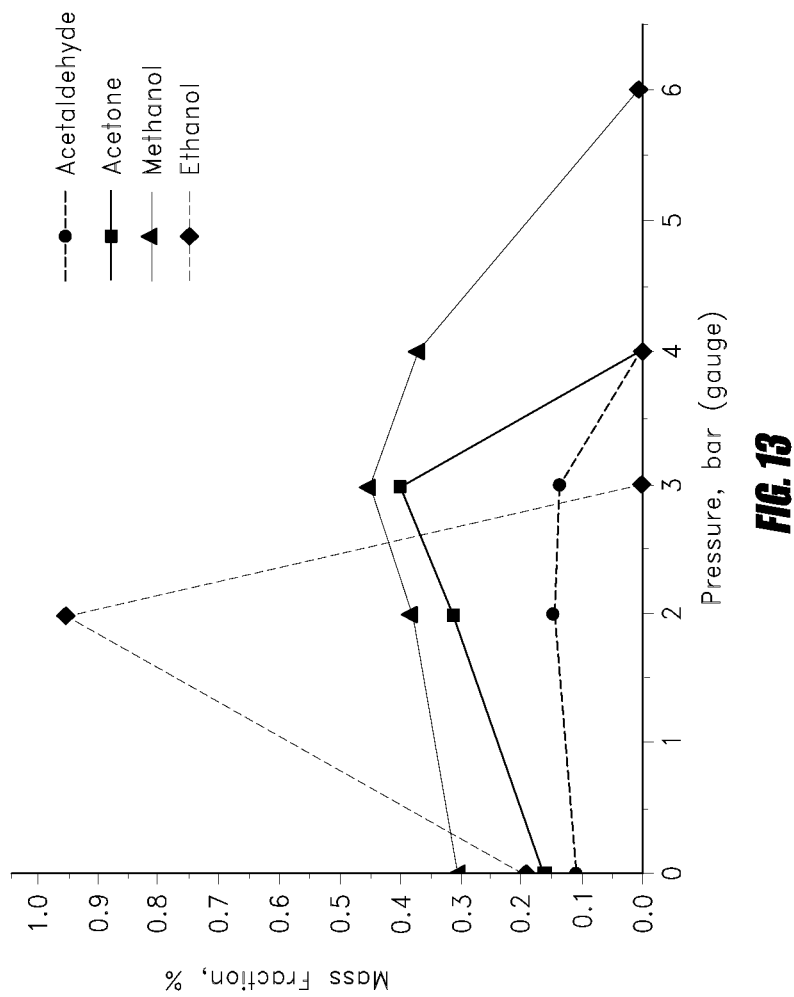
FIG. 13 is a graph of the relative concentrations for acetaldehyde, acetone, methanol and ethanol in the condensed product stream for reaction at different pressures in the conversion of glycerol to monohydric alcohols by sequential dehydration and hydrogenation with intermediate addition of hydrogen at different pressures in the reactor set-up of FIG. 1.
Figure 14:
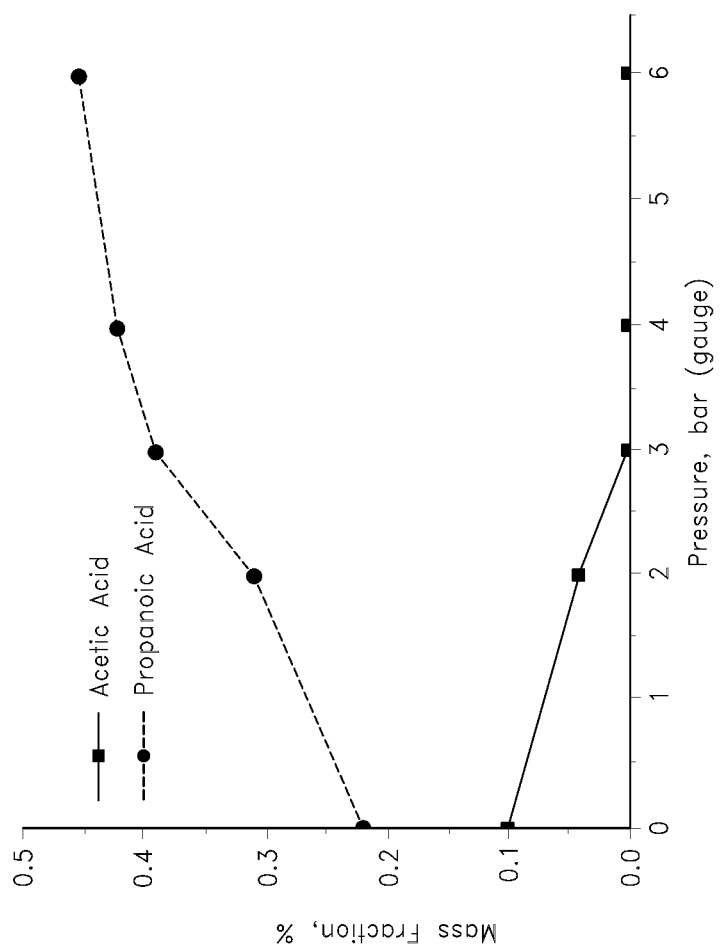
FIG. 14 is a graph of the relative concentrations of acetic acid and propanoic acid for reaction at different pressures in the condensed product stream for the conversion of glycerol to monohydric alcohols by sequential dehydration and hydrogenation with intermediate addition of hydrogen at different pressures in the reactor set-up of FIG. 1.

Analytical results for acetaldehyde, acetone, methanol, and ethanol are shown in FIG. 13. This graph shows that under these reaction conditions, alcohol selectivity for 1-propanol increases up to about 4 bar (gauge). Analytical results for acetic acid and propanoic acid in the product stream are shown in FIG. 14.

EXAMPLE 5

Figure 15:
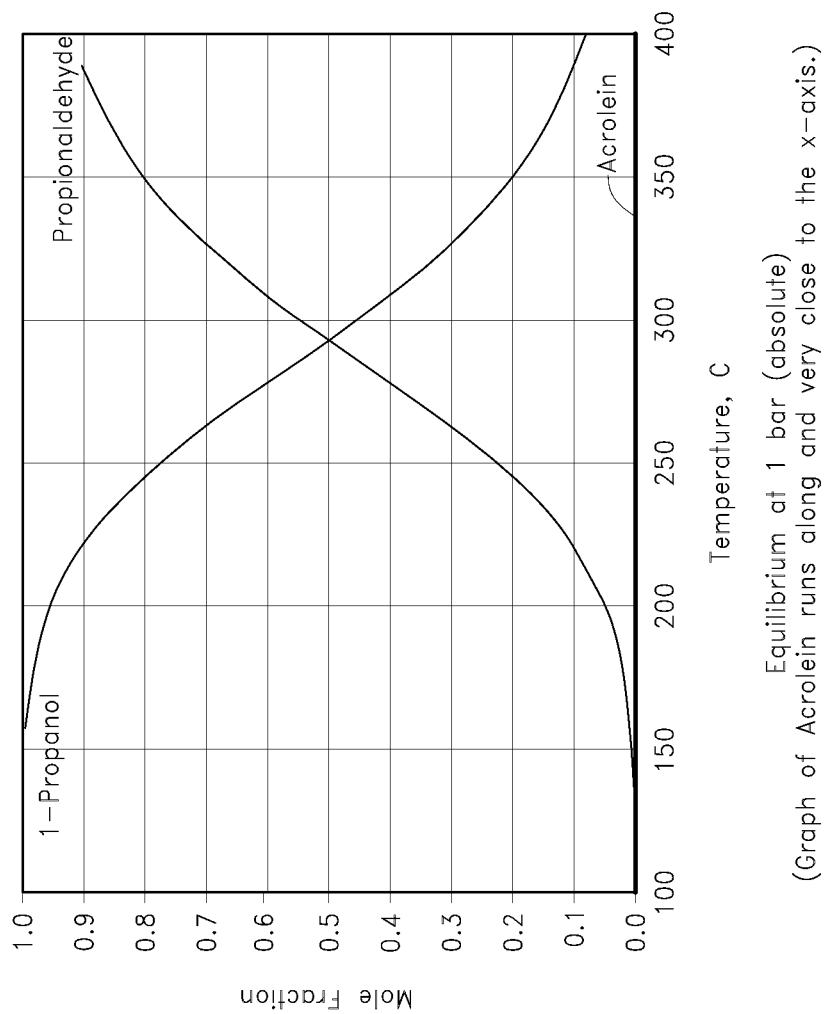
FIG. 15 is a graph of the equilibrium between propionaldehyde, 1-propanol and acrolein at 1 bar for the sequential dehydration-hydrogenation reaction system at different temperatures. This figure shows the condensed phase concentrations for the reacted products at 1 bar.
Figure 16:
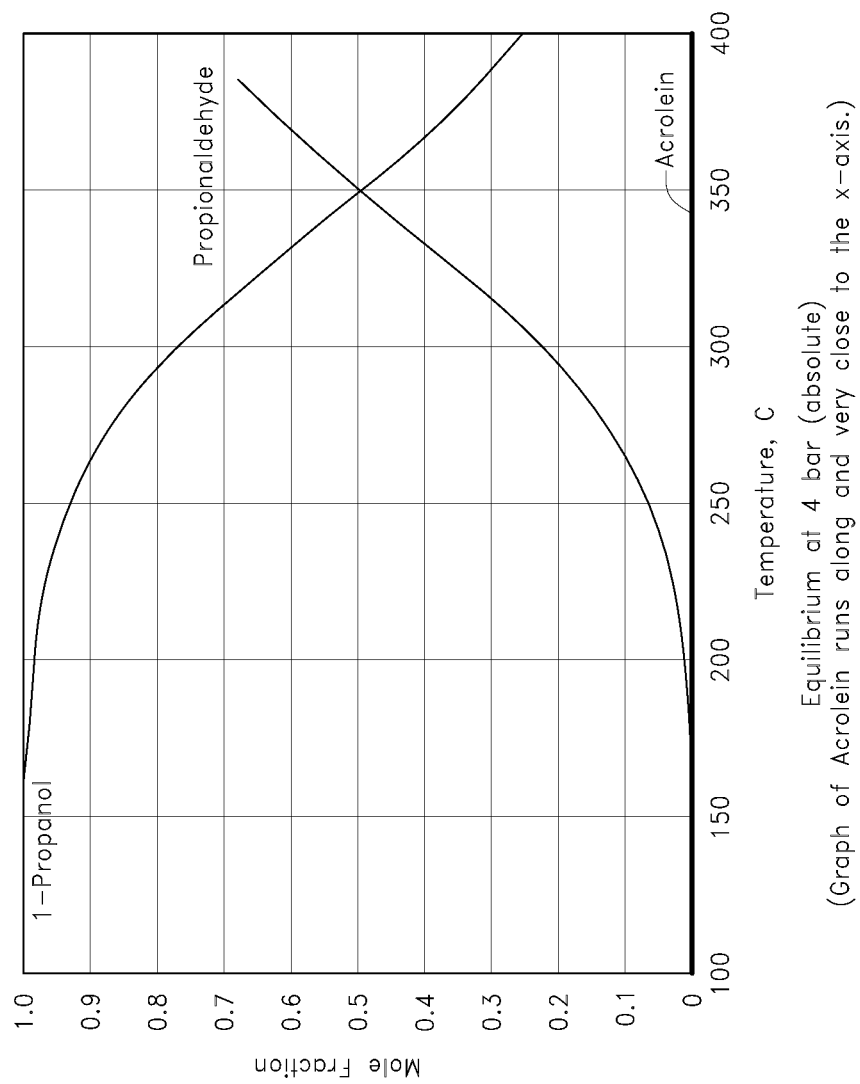
FIG. 16 is a graph of the equilibrium between propionaldehyde, 1-propanol and acrolein at 4 bar for the sequential dehydration-hydrogenation reaction system at different temperatures. This figure shows higher 1-propanol concentration at a given temperature than at 1 bar, in FIG. 15.

The temperature and pressure dependence of the propionaldehyde/1-propanol/acrolein equilibrium were determined using a free energy analysis for a reaction mixture of 1 mole acrolein, 25 moles water, and 150 moles hydrogen at 1 bar (absolute) and 4 bar (absolute) and various temperatures are shown in FIGS. 15 and 16. These graphs show that as the temperature increased, there is less 1-propanol and more propionaldehyde present at equilibrium. In addition, as pressures increased the equilibrium shifted to the right, resulting in more 1-propanol, and less propionaldehyde.

While it is generally preferred to operate the process according to the sequence of steps as depicted in the figures, in alternative embodiments the steps can be conducted in different order, or combined. For example, the two reaction steps can be done prior to any substantial separation step, or the two separation steps may be combined into one overall separation step. Additional processing can also be performed on the monohydric alcohol rich stream to purify it, to separate various alcohols, to remove water, to react the alcohols, to combine it with other materials, or any combination of these additional processing steps. For example, in one embodiment, the monohydric alcohol rich stream can be treated to remove at least some of the residual water and then combined with a diesel or biodiesel material. In another embodiment, the monohydric alcohol rich stream may be treated to remove at least some residual water and then esterified, or transesterified to fatty acids.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will be apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for converting glycerol to monohydric alcohol, the method comprising:
    reacting a gaseous mixture comprising glycerol, water and hydrogen in a first reaction bed comprising a heterogeneous catalyst system comprising a dehydration catalyst and a hydrogenation catalyst, whereby a first reacted mixture is produced, the first reaction mixture comprising propionaldehyde;
    separating at least a portion of the first reacted mixture into a more volatile fraction and a less volatile fraction in a first condenser;
    reacting a mixture of hydrogen and at least a portion of the more volatile fraction from the first reacted mixture in a second reactor bed comprising a hydrogenation catalyst, whereby a second reacted mixture comprising a monohydric alcohol is produced;
    separating at least a portion of the second reacted mixture into a less volatile fraction comprising a monohydric alcohol and a more volatile fraction in a second condenser.

2. The method of claim 1, further comprising introducing at least a portion of the less volatile fraction of the first reacted mixture into the first reaction bed.

3. The method of claim 1, further comprising introducing at least a portion of the less volatile fraction of the second reacted mixture into the second reaction bed.

4. The method of claim 2, further comprising volatilizing at least a portion of the less volatile fraction of the first reacted mixture prior to introducing it into the first reaction bed.

5. The method of claim 3, further comprising volatilizing at least a portion of the less volatile fraction of the second reacted mixture prior to introducing it into the second reaction bed.

6. The method of claim 1, wherein the first reaction bed catalyzes dehydration reactions requiring heat and hydrogenation reactions generating heat, wherein the heat required by the dehydration reactions approximately balances the heat generated by the hydrogenation reactions.

7. The method of claim 6, wherein an absolute value of the heat required by the dehydration reactions is provided by an absolute value of the heat generated by the hydrogenation reactions.

8. The method of claim 6, wherein an absolute value of the heat generated by the hydrogenation reactions provides an absolute value of the heat required by the dehydration reactions and other processes.

9. The method of claim 6, wherein the heat required by the dehydration reactions and the heat generated by the hydrogenation reaction are balanced by controlling a ratio of an amount of dehydration catalyst to hydrogenation catalyst in the first reaction bed.

10. The method of claim 6, wherein the heat required by the dehydration reactions and the heat generated by the hydrogenation reactions are balanced by controlling an amount of hydrogen present in the gaseous mixture.

11. The method of claim 6, wherein the heat required by the dehydration reactions and the heat generated by the hydrogenation reactions are balanced by controlling a ratio of hydrogen to glycerol.

12. The method of claim 11, wherein a molar ratio of hydrogen to glycerol in the gaseous mixture is from about 0.05:10 to about 10:10.

13. The method of claim 11, wherein a molar ratio of hydrogen to glycerol in the gaseous mixture is from about 0.1:10 to about 2:10.

14. The method of claim 1, wherein the heterogeneous catalyst system has a selectivity for conversion of glycerol to acrolein, the selectivity being greater than about 75 (wt.) %.

15. The method of claim 1, wherein the heterogeneous catalyst system has a selectivity for conversion of glycerol to acrolein, the selectivity being greater than about 85 (wt.) %.

16. The method of claim 1, wherein the heterogeneous catalyst system has a selectivity for conversion of glycerol to acrolein, the selectivity being dependent on the catalysts present, the time for the reaction, the temperature of the reaction, and the pressure of the reaction, the selectivity being greater than about 95 (wt.) %.

17. The method of claim 1, wherein the heterogeneous catalyst system has a selectivity for conversion of acrolein to propionaldehyde, the selectivity being greater than about 65 (wt.) %.

18. The method of claim 1, wherein the heterogeneous catalyst system has a selectivity for conversion of acrolein to propionaldehyde, the selectivity being greater than about 75 (wt.) %.

19. The method of claim 1, wherein the heterogeneous catalyst system has a selectivity for conversion of acrolein to propionaldehyde, the selectivity being greater than about 85 (wt.) %.

20. The method of claim 1, wherein the heterogeneous catalyst system has a selectivity for conversion of propionaldehyde to propanol, the selectivity being less than about 25 (wt.) %.

21. The method of claim 1, wherein the heterogeneous catalyst system has a selectivity for conversion of propionaldehyde to propanol, the selectivity being less than about 15 (wt.) %.

22. The method of claim 1, wherein the heterogeneous catalyst system has a selectivity for conversion of propionaldehyde to propanol, the selectivity being less than about 5 (wt.) %.

23. The method of claim 1, wherein the first reacted mixture comprising at least one carbonyl contains less than about 10 mol % of a monohydric alcohol.

24. The method of claim 1, wherein the first reacted mixture comprising at least one carbonyl contains less than about 3 mol % of a monohydric alcohol.

25. The method of claim 1, wherein the first reacted mixture comprising at least one carbonyl compound comprises monohydric alcohol and propionaldehyde present in a weight ratio of from about 0:10 to about 3:7.

26. The method of claim 1, wherein the first reacted mixture comprising at least one carbonyl compound comprises monohydric alcohol and propionaldehyde present in a weight ratio of from about 0.1:10 to about 1:9.

* * * * *